(12) United States Patent
Thompson

(10) Patent No.: US 12,416,020 B2
(45) Date of Patent: Sep. 16, 2025

(54) PLASMID ENCODING A TLR3 AND Fc FUSION PROTEIN

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/582,222

(22) Filed: Feb. 20, 2024

(65) Prior Publication Data
US 2025/0263739 A1     Aug. 21, 2025

(51) Int. Cl.
| | |
|---|---|
| C12N 15/00 | (2006.01) |
| C07K 14/48 | (2006.01) |
| C07K 14/62 | (2006.01) |
| C07K 14/705 | (2006.01) |
| C12N 9/22 | (2006.01) |
| C12N 15/86 | (2006.01) |

(52) U.S. Cl.
CPC .............. *C12N 15/86* (2013.01); *C07K 14/48* (2013.01); *C07K 14/62* (2013.01); *C07K 14/705* (2013.01); *C07K 14/70596* (2013.01); *C12N 9/22* (2013.01); *C07K 2319/30* (2013.01); *C12N 2750/14143* (2013.01); *C12N 2800/00* (2013.01)

(58) Field of Classification Search
None
See application file for complete search history.

(56) References Cited

U.S. PATENT DOCUMENTS

| | | |
|---|---|---|
| 8,841,416 B2 | 9/2014 | Ledbetter |
| 11,085,055 B2 | 8/2021 | Mallol et al. |
| 11,162,102 B2 | 11/2021 | Minshull et al. |
| 11,359,001 B2 | 6/2022 | Lancaster |
| 11,530,423 B1 | 12/2022 | Thompson |
| 11,873,505 B2 * | 1/2024 | Thompson .............. C12N 15/86 |
| 11,976,104 B2 * | 5/2024 | Wei ................... G01N 33/57488 |
| 12,018,274 B2 | 6/2024 | Thompson |
| 12,134,770 B1 | 11/2024 | Thompson |
| 12,180,521 B2 | 12/2024 | Ledbetter |
| 2003/0104523 A1 * | 6/2003 | Bauer ..................... A61P 37/00 435/6.16 |
| 2021/0253664 A1 * | 8/2021 | Wei ....................... C07K 14/705 |
| 2024/0026377 A1 | 1/2024 | Thompson |
| 2025/0002884 A1 | 1/2025 | Posada |
| 2025/0011445 A1 | 1/2025 | Bergmann |

FOREIGN PATENT DOCUMENTS

| | | |
|---|---|---|
| CA | 2721333 A1 | 10/2009 |
| CN | 114829384 | 7/2022 |
| IN | P202305938 | 7/2023 |
| KR | 100808908 B1 | 3/2008 |
| WO | WO-2004096156 A2 * | 11/2004 ......... C07K 16/2896 |
| WO | WO-2020041590 A1 * | 2/2020 .............. A61P 35/00 |
| WO | 2021168413 A1 | 8/2021 |
| WO | 2022074236 A2 | 4/2022 |
| WO | 2022178078 A1 | 8/2022 |
| WO | 2023051412 A1 | 4/2023 |
| WO | 2023088351 A1 | 5/2023 |
| WO | 2024107701 A2 | 5/2024 |

(Continued)

OTHER PUBLICATIONS

O'Brien et al. "Overview of microRNA biogenesis, mechanisms of actions, and circulation." Frontiers in endocrinology 9 (2018): 402.
Gorski et al. "RNA-based recognition and targeting: sowing the seeds of specificity." Nature Reviews Molecular Cell Biology 18.4 (2017): 215-228.
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.

(Continued)

*Primary Examiner* — Michael C Wilson
(74) *Attorney, Agent, or Firm* — Gowling WLG (Canada) LLP

(57) ABSTRACT

Loss of B cell tolerance and generation of autoreactive anti-nuclear antibodies are hallmarks of systemic lupus erythematosus (SLE) and lupus nephritis. Lupus nephritis is characterized by glomerular and tubulointerstitial inflammation often initiated by the renal glomerular deposition of anti-nuclear immune complexes which trigger subsequent activation of complement, macrophages/monocytes and other innate inflammatory cells. The mechanism of anti-nuclear immunoglobulin accumulation and clearance in lupus nephritis pathogenesis remains largely uncharacterized. Here, we show that innate immune activation in the NZB/W F1 mouse model and in human lupus nephritis biopsies rapidly reduces DNase1 expression in renal cortex proximal tubular cells. To overcome the loss of endogenous DNase1, we treated lupus-prone mice with a hyperactive actin resistant variant of DNase1 with improved catalytic activity against nucleic acid-IgG immune complexes and acceptable in vivo pharmacokinetics. Hyperactive DNase1-Fc fusion protein ameliorates nephritis in a murine model of lupus nephritis and reduces immune complex deposition/complement fixation. Taken together, our data suggest that the loss of renal DNase1 through TLR signaling or other innate immune activation impairs clearance of autoreactive anti-nuclear immune complex deposits in the kidney to promote nephritis progression. Our findings provide a therapeutic rationale for using an engineered DNase1-Fc as a potential therapeutic approach in lupus nephritis.

3 Claims, No Drawings

Specification includes a Sequence Listing.

(56) References Cited

FOREIGN PATENT DOCUMENTS

WO     202419137 A2     9/2024

OTHER PUBLICATIONS

Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
Wang et al. "Adeno-associated virus vector as a platform for gene therapy delivery." Nature reviews Drug discovery 18.5 (2019): 358-378.
Kondratov et al. "Direct head-to-head evaluation of recombinant adeno-associated viral vectors manufactured in human versus insect cells." Molecular Therapy 25.12 (2017): 2661-2675.
Nature (2010. Gene Expression. Scitable. Available online at Nature.com) <https://www.nature.com/scitable/topicpage/gene-expression-14121669> (2010).
Brutons Tyrosine Kinase Genbank Sequence (2023).
GenBank EGFR Sequence (2023).
GenBank EGF Sequence (2023).
NCBI search results for Seq ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
NCBI Nucleotide Sequence for PARP, search performed Dec. 26, 2024 (2024).
GenBank FLT3 Sequence (2024).
Dwyer et al. (J. Biol. Chem. 274:9738-43, 1999) (Year: 1999).
Mei et al. Chapter 7 Monomeric Fc-Fusion Proteins. First published: Feb. 12, 2013 https://doi.org/10.1002/9781118354599.ch7 (Year: 2013).
Mouchess et al. A rationally engineered DNase1-Fc fusion protein ameliorates autoimmune glomerulonephritis. Journal of Immunology, (May 1, 2019) vol. 202, No. 1, Suppl. S, pp. 132.4. (Year: 2019).
Austin et al. A Rationally Engineered Hyperactive Actin-Resistant DNase1-Fc Fusion Protein Ameliorates Autoimmune Glomerulonephritis. FASEB Journal, (Apr. 2019) vol. 33, No. Suppl. 1, pp. 802.10. (Year: 2019).

\* cited by examiner

SEQUENCE LISTING

```
Sequence total quantity: 11
SEQ ID NO: 1            moltype = DNA   length = 5861
FEATURE                 Location/Qualifiers
source                  1..5861
                        mol_type = other DNA
                        organism = synthetic construct
SEQUENCE: 1
ttctagaata atcaacctct ggattacaaa atttgtgaaa gattgactgg tattcttaac   60
tatgttgctc cttttacgct atgtggatac gctgctttaa tgcctttgta tcatgctatt  120
gcttcccgta tggctttcat tttctcctcc ttgtataaat cctggttgct gtctctttat  180
gaggagttgt ggcccgttgt caggcaacgt ggcgtggtgt gcactgtgtt tgctgacgca  240
accccactg gttggggcat tgccaccacc tgtcagctcc tttccgggac tttcgctttc   300
cccctccta ttgccacggc ggaactcatc gccgcctgcc ttgcccgctg ctggacaggg   360
gctcggctgt tgggcactga caattccgtg gtgttgtcgg ggaaatcatc gtcctttcct  420
tggctgctcg cctgtgttgc cacctggatt ctgcgcggga cgtccttctg ctacgtccct  480
tcggccctca atccagcgga ccttccttcc cgcggcctgc tgccggctct gcggcctctt  540
ccgcgtcttc gccttcgccc tcagacgagt cggatctccc tttgggccgc ctcccccgcct 600
aagcttatcg ataccgtcga gatctaactt gtttattgca gcttataatg gttacaaata  660
aagcaatagc atcacaaatt tcacaaataa agcattttt tcactgcatt ctagttgtgg  720
tttgtccaaa ctcatcaatg tatcttatca tgtctggatc tcgacctcga ctagagcatg  780
gctacgtaga taagtagcat ggcgggttaa tcattaacta caaggaaccc ctagtgatgg  840
agttggccac tccctctctg cgcgctcgct cgctcactga ggccgggcga ccaaaggtcg  900
cccgacgccc gggctttgcc cgggcggcct cagtgagcga gcgagcgcgc cagctggcgt  960
aatagcgaag aggcccgcac cgatcgccct tcccaacagt tgcgcagcct gaatggcgaa 1020
tggaattcca gacgattgag cgtcaaaatg taggtatttc catgagcgtt tttcctgttg 1080
caatggctgg cggtaatatt gttctggata ttaccagcaa ggccgatagt ttgagttctt 1140
ctactcaggc aagtgatgtt attactaatc aaagaagtat tgcgacaacg gttaatttgc 1200
gtgatggaca gactctttta ctcggtggcc tcactgatta taaaaacact tctcaggatt 1260
ctggcgtacc gttcctgtct aaaatccctt taatcggcct cctgtttagc tcccgctctg 1320
attctaacga ggaaagcacg ttatacgtgc tcgtcaaagc aaccatagta cgcgccctgt 1380
agcggcgcat taagcgcggc gggtgtggtg gttacgcgca gcgtgaccgc tacacttgcc 1440
agcgccctag cgcccgctcc tttcgctttc ttcccttcct ttctcgccac gttcgccggc 1500
tttccccgtc aagctctaaa tcgggggctc cctttagggt tccgatttag tgctttacgg 1560
cacctcgacc ccaaaaaact tgattagggt gatggttcac gtagtgggcc atcgccctga 1620
tagacggttt ttcgcccttt gacgttggag tccacgttct ttaatagtgg actcttgttc 1680
caaactggaa caacactcaa ccctatctcg gtctattctt ttgatttata agggattttg 1740
ccgatttcgg cctattggtt aaaaaatgag ctgatttaac aaaaatttaa cgcgaatttt 1800
aacaaaatat taacgtttac aatttaaata tttgcttata caatcttcct gtttttggggg 1860
cttttctgat tatcaaccgg ggtacatatg attgacatgc tagttttacg attaccgttc 1920
atcgattctc ttgtttgctc cagactctca ggcaatgacc tgatagcctt tgtagagacc 1980
tctcaaaaat agctaccctc tccggcatga atttatcagc tagaacggtt gaatatcata 2040
ttgatggtga tttgactgtc tccggccttt ctcacccgtt tgaatcttta cctacacatt 2100
actcaggcat tgcatttaaa atatatgagg gttctaaaaa tttttatcct tgcgttgaaa 2160
taaaggcttc tcccgcaaaa gtattacagg gtcataatgt ttttggtaca accgatttag 2220
ctttatgctc tgaggcttta ttgcttaatt ttgctaattc tttgccttgc ctgtatgatt 2280
tattggatgt tggaattcct gatgcggtat tttctcctta cgcatctgtg cggtatttca 2340
caccgcatat ggtgcactct cagtacaatc tgctctgatg ccgcatagtt aagccagccc 2400
```

```
cgacacccgc caacacccgc tgacgcgccc tgacgggctt gtctgctccc ggcatccgct    2460
tacagacaag ctgtgaccgt ctccgggagc tgcatgtgtc agaggttttc accgtcatca    2520
ccgaaacgcg cgagacgaaa gggcctcgtg atacgcctat tttttataggt taatgtcatg    2580
ataataatg tttcttagac gtcaggtggc acttttcggg gaaatgtgcg cggaacccct    2640
atttgtttat ttttctaaat acattcaaat atgtatccgc tcatgagaca ataaccctga    2700
taaatgcttc aataatattg aaaaaggaag agtatgagta ttcaacattt ccgtgtcgcc    2760
cttattccct tttttgcggc attttgcctt cctgtttttg ctcacccaga aacgctggtg    2820
aaagtaaaag atgctgaaga tcagttgggt gcacgagtgg gttacatcga actggatctc    2880
aacagcggta agatccttga gagttttcgc cccgaagaac gttttccaat gatgagcact    2940
tttaaagttc tgctatgtgg cgcggtatta tcccgtattg acgccgggca agagcaactc    3000
ggtcgccgca tacactattc tcagaatgac ttggttgagt actcaccagt cacagaaaag    3060
catcttacgg atggcatgac agtaagagaa ttatgcagtg ctgccataac catgagtgat    3120
aacactgcgg ccaacttact tctgacaacg atcggaggac cgaaggagct aaccgctttt    3180
ttgcacaaca tgggggatca tgtaactcgc cttgatcgtt gggaaccgga gctgaatgaa    3240
gccataccaa acgacgagcg tgacaccacg atgcctgtag caatggcaac aacgttgcgc    3300
aaactattaa ctggcgaact acttactcta gcttcccggc aacaattaat agactggatg    3360
gaggcggata aagttgcagg accacttctg cgctcggccc ttccggctgg ctggtttatt    3420
gctgataaat ctggagccgg tgagcgtggg tctcgcggta tcattgcagc actggggcca    3480
gatggtaagc cctcccgtat cgtagttatc tacacgacgg ggagtcaggc aactatggat    3540
gaacgaaata gacagatcgc tgagataggt gcctcactga ttaagcattg gtaactgtca    3600
gaccaagttt actcatatat actttagatt gatttaaaac ttcatttta atttaaaagg    3660
atctaggtga agatcctttt tgataatctc atgaccaaaa tcccttaacg tgagttttcg    3720
ttccactgag cgtcagaccc cgtagaaaag atcaaaggat cttcttgaga tcctttttt    3780
ctgcgcgtaa tctgctgctt gcaaacaaaa aaaccaccgc taccagcggt ggtttgtttg    3840
ccggatcaag agctaccaac tcttttccg aaggtaactg gcttcagcag agcgcagata    3900
ccaaatactg tccttctagt gtagccgtag ttaggccacc acttcaagaa ctctgtagca    3960
ccgcctacat acctcgctct gctaatcctg ttaccagtgg ctgctgccag tggcgataag    4020
tcgtgtctta ccgggttgga ctcaagacga tagttaccgg ataaggcgca gcggtcgggc    4080
tgaacgggg gttcgtgcac acagcccagc ttggagcgaa cgacctacac cgaactgaga    4140
tacctacagc gtgagctatg agaaagcgcc acgcttcccg aagggagaaa ggcggacagg    4200
tatccggtaa gcggcagggt cggaacagga gagcgcacga gggagcttcc agggggaaac    4260
gcctggtatc tttatagtcc tgtcgggttt cgccacctct gacttgagcg tcgatttttg    4320
tgatgctcgt caggggggcg gagcctatgg aaaaacgcca gcaacgcggc ctttttacgg    4380
ttcctggcct tttgctggcc ttttgctcac atgttcttc ctgcgttatc ccctgattct    4440
gtggataacc gtattaccgc ctttgagtga gctgataccg ctcgccgcag ccgaacgacc    4500
gagcgcagcg agtcagtgag cgaggaagcg gaagagcgcc caatacgcaa accgcctctc    4560
cccgcgcgtt ggccgattca ttaatgcagc agctgcgcgc tcgctcgctc actgaggccg    4620
cccgggcaaa gcccgggcgt cgggcgacct ttggtcgccc ggcctcagtg agcgagcgag    4680
cgcgcagaga gggagtggcc aactccatca ctaggggttc cttgtagtta atgattaacc    4740
cgccatgcta cttatctacg tagccatgct ctaggacatt gattattgac tagtggagtt    4800
ccgcgttaca taacttacgg taaatggccc gcctggctga cgccccaacg acccccgccc    4860
attgacgtca ataatgacgt atgttcccat agtaacgcca atagggactt tccattgacg    4920
tcaatgggtg gagtatttac ggtaaactgc ccacttggca gtacatcaag tgtatcatat    4980
gccaagtacg ccccctattg acgtcaatga cggtaaatgg cccgcctggc attatgccca    5040
gtacatgacc ttatgggact ttcctacttg gcagtacatc tacgtattag tcatcgctat    5100
taccatggtc gaggtgagcc cacgttctg cttcactctc cccatctccc cccctcccc    5160
acccccaatt ttgtatttat ttatttttta attatttgt gcagcgatgg gggcggggg    5220
ggggggggc gcgcgccagg cggggcgggg cggggcgagg ggcggggcgg ggcgaggcgg    5280
agaggtgcgg cggcagccaa tcagagcggc gcgctccgaa agtttccttt tatggcgagg    5340
cggcggcggc ggcggcccta taaaagcga agcgcgcggc gggcgggagt cgctgcgcgc    5400
tgccttcgcc ccgtgccccg ctccgccgcc gcctcgcgcc gcccgccccg gctctgactg    5460
accgcgttac taaaacaggt aagtccggcc tccgcgccgg gttttggcgc ctcccgcggg    5520
cgcccccctc ctcacggcga gcgctgccac gtcagacgaa gggcgcagcg agcgtcctga    5580
tccttccgcc cggacgctca ggacagcggc ccgctgctca taagactcgg ccttagaacc    5640
ccagtatcag cagaaggaca ttttaggacg ggacttggtt gactctaggg cactggtttt    5700
ctttccagag agcggaacag gcgaggaaaa gtagtcccctt ctcggcgatt ctgcggaggg    5760
atctccgtgg ggcggtgaac gccgatgatg cctctactaa ccatgttcat gttttctttt    5820
tttttctaca ggtcctgggt gacgaacagg gtaccgccac c                        5861

SEQ ID NO: 2           moltype = DNA   length = 1560
FEATURE                Location/Qualifiers
source                 1..1560
                       mol_type = other DNA
                       organism = synthetic construct
SEQUENCE: 2
atgaggggca tgaagctgct ggggggcgctg ctggcactgg cggccctact gcaggggggcc     60
gtgtccctga agatcgcagc cttcaacatc cagacatttg gggagaccaa gatgtccaat    120
gccaccctcg tcagctacat tgtgcagatc ctgagccgct atgacatcgc cctggtccag    180
gaggtcagag acagccacct gactgccgtg gggaaacct tggcaacct caatcaggat    240
gcaccagaca cctatcacta cgtggtcagt gagccactgg gacggaacag ctataaggag    300
cgctacctgt tcgtgtacag gcctgaccag gtgtctgcgg tggacagcta ctactacgat    360
gatggctgcg agccctgcgg gaacgacacc ttcaaccgag agccagccat gtcaggttc    420
ttctcccggt tcacagaggt cagggagttt gccattgttc cctgcatgc ggccccgggg    480
gacgcagtag ccgagatcga cgctctctat gacgtctcca gagaaatgg    540
ggcttggagg acgtcatgtt gatgggcgac ttcaatgcgg gctgcagcta tgtgagaccc    600
tcccagtggt catccatccg cctgtggaca agccccacct tccagtggct gatccccgac    660
agcgctgaca ccacagctac acccacgcac tgtgcctatg acaggatcgt ggttgcaggg    720
atgctgctcc gaggcgccgt tgttcccgac tcggctcttc cctttaactt ccaggctgcc    780
tatgccctga gtgaccaact ggcccaagcc atcagtgacc actatccagt ggaggtgatg    840
```

```
ctgaagggcg gatcaggcgg atcacccaaa tcttgtgaca aaactcacac atgcccaccg    900
tgcccagcac ctgaactcct gggggggaccg tcagtcttcc tcttcccccc aaaacccaag    960
gacacccttca tgatctcccg gacccctgag gtcacatgcg tggtggtgga cgtgagccac   1020
gaagaccctg aggtcaagtt caactggtac gtggacggcg tggaggtgca taatgccaag   1080
acaaagccgc gggaggagca gtacaacagc acgtaccgtg tggtcagcgt cctcaccgtc   1140
ctgcaccagg actggctgaa tggcaaggag tacaagtgca aggtctccaa caaagccctc   1200
ccagccccca tcgagaaaac catctccaaa gccaaagggc agccccgaga accacaggtg   1260
tacaccctgc ccccatcccg ggaggagatg accaagaacc aggtcagcct gacctgcctg   1320
gtcaaaggct tctatcccag cgacatcgcc gtggagtggg agagcaatgg gcagccggag   1380
aacaactaca agaccacgcc tcccgtgctg gactccgacg gctccttctt cctctacagc   1440
aagctcaccg tggacaagag caggtggcag caggggaacg tcttctcatg ctccgtgatg   1500
catgaggctc tgcacaacca ctacacgcag aagagcctct ccctgtctcc gggtaaatag   1560

SEQ ID NO: 3          moltype = DNA  length = 3423
FEATURE               Location/Qualifiers
source                1..3423
                      mol_type = other DNA
                      organism = synthetic construct
SEQUENCE: 3
gccagaccct gccgtgcatt tattttttggg gcggcctgct gccgtttggc atgctgtgcg     60
cgagcagcac caccaaatgc accgtgagcc atgaagtggc ggattgcagc catctgaaac    120
tgacccaggt gccggatgat ctgccgacca acattaccgt gctgaacctg acccataacc    180
agctgcgccg cctgccggcg gcgaacttta cccgctatag ccagctgacc agcctggatg    240
tgggctttaa caccattagc aaactggaac cggaactgtg ccagaaactg ccgatgctga    300
aagtgctgaa cctgcagcat aacgaactga gccagctgag cgataaaacc tttgcgtttt    360
gcaccaacct gaccgaactg catctgatga gcaacaatga tcagaaaatt aaaaaacaacc    420
cgtttgtgaa acagaaaaac ctgattaccc tggatctgaa ccataacggc ctgagcagca    480
ccaaactggg cacccaggtg cagctggaaa acctgcagga actgctgctg agcaacaaca    540
aaattcaggc gctgaaaagc gaagaactgg atattttttgc gaacagcagc ctgaaaaaac    600
tggaactgag cagcaaccag attaaagaat ttagcccagg ctgctttcat gcgattgcc    660
gcctgtttgg cctgtttctg aacaacgtgc agctgggccc gagcctgacc gaaaaactgt    720
gcctggaact ggcgaacacc agcattcgca acctgagcct gagcaacagc cagctgagca    780
ccaccagcaa caccaccttt ctgggcctga atggaccaa cctgaccatg ctggatctga    840
gctataacaa cctgaacgtg gtgggcaacg atagcttttgc gtggctgccg cagctggaat    900
atttttttct ggaatataac aacattcagc atctgtttta ccatagcctg catgcctgt    960
ttaacgtgcg ctatctgaac ctgaaacgca gctttaccaa acagagcatt agcctgccga   1020
gcctgccgaa aattgatgat tttagctttc agtggctgaa atgcctggaa catctgaaca   1080
tggaagataa cgatattccg ggcattaaaa gcaacatgtt taccggcctg attaacctga   1140
aatatctgag cctgagcaac agctttacca gcctgcgcac cctgaccaac gaaaccttg    1200
tgagcctggc gcatagcccg ctgcatattc tgaacctgac caaaaacaaa attagcaaaa   1260
ttgaaagcga tgccgtttagc tggctgggcc atctggaagt gctggatctg ggcctgaacg   1320
aaaattggcca ggaactgacc ggccaggaat ggcgcggcct ggaaaacatt tttgaaattt   1380
atctgagcta taacaaatat ctgcagctga cccgcaacga ctttgcgctg gtgccgacc   1440
tgcagcgcct gatgctgcgc cgcgtggcgc tgaaaaacgt ggatagcagc ccgagcccgt   1500
ttcagccgct cgcgcaacctg accattctgg atctgagcaa caacaacatt gcgaacatta   1560
acgatgatat gctggaaggc ctggaaaaac tggaattctct ggatctgcag cataacaacc   1620
tggcgcgcct gtggaaacat gcgaacccgg gcggcccgat ttattttctg aaaggcctga   1680
gccatctgca tattctgaac ctggaaagca acggcttttga tgaaattccg gtggaagtgt   1740
ttaaagatct gtttgaactg aaaattattg atctgggcct gaacaacctg aacaccctgc   1800
cggcgagcgt gtttaacaac caggtgagcc tgaaaagcct gaacctgcag aaaaacctga   1860
ttaccagcgt ggaaaaaaaa gtgtttggcc cggcgtttgc caacctgacc gaactggata   1920
tgcgctttaa cccgtttgat tgcacctgcg aaagcattgc gtggtttgtg aactggatta   1980
acgaaaccca taccaacatt ccggaactga gcagccatta tctgtgcaac ccccgccgc   2040
attatcatgc ctttccggtg cgcctgtttg ataccagcag ctgcaaagat agcgcgccgt   2100
ttgaactgtt aacaccagca ttctgctgtt ttttattttt attgtgctgc   2160
tgattcattt tgaaggctgg cgcattagct tttattggaa cgtgagcgtg catcgcgtgc   2220
tgggctttaa agaaattgat cgccagaccg aacagtttga atatgcggcg tatattattc   2280
atgcgtataa agataaagat tgggtgtggg aacattttag cagcatgaa aaagaagatc   2340
agagcctgaa attttgcctg gaagaacgcg attttgaagc gggcgtgttt gaactggaag   2400
cgattgtgaa cagcagccga aaattatttt tgtgattacc catcatctgc   2460
tgaaagatcc gctgtgcaaa cgctttaaag tgcatcatgc ggtgcagcag gcgattgaac   2520
agaacctgga tagcattatt ctggtgtttc tggaagaaat tccggattat aaactgaacc   2580
atgcgctgtg cctgcgccgc ggcatgttta aagccattg cattctgaac tggccggtgc   2640
agaaagaacg cattgcgcg tttcgccata aactgcaggt ggcgctgggc gcaaaaaca   2700
gcgtgcatgg gcggatcagg cggatcaccc aaatcttgtg acaaaactca cacatgccca   2760
ccgtgcccag cacctgaact cctggggggga ccgtcagtct tcctcttccc cccaaaaccc   2820
aaggacaccc tcatgatctc ccggacccct gaggtcacat gcgtggtggt ggacgtgagc   2880
cacgaagacc ctgaggtcaa gttcaactgg tacgtggacg gcgtggaggt gcataatgcc   2940
aagacaaagc cgcgggagga gcagtacaac agcacgtacc gtgtggtcag cgtcctcacc   3000
gtcctgcacc aggactggct gaatggcaag gagtacaagt gcaaggtctc caacaaagcc   3060
ctcccagccc ccatcgagaa aaccatctcc aaagccaaag gcagcccg agaaccacag   3120
gtgtacaccc tgcccccatc ccgggaggag atgaccaaga ccaggtcag cctgacctgc   3180
ctggtcaaag gcttctatcc cagcgacatc gccgtggagt gggagagcaa tgggcagccg   3240
gagaacaact acaagaccac gcctcccgtg ctggactccg acggctcctt cttcctctac   3300
agcaagctca ccgtggacaa gagcaggtgg cagcagggga acgtcttctc atgctccgtg   3360
atgcatgagg ctctgcacaa ccactacacg cagaagagcc tctccctgtc tccgggtaaa   3420
tag                                                                3423

SEQ ID NO: 4          moltype = DNA  length = 3877
```

| FEATURE | Location/Qualifiers |
|---|---|
| source | 1..3877 |
| | mol_type = other DNA |
| | organism = synthetic construct |

SEQUENCE: 4

```
atgaggggca tgaagctgct gggggcgctg ctggcactgg cggccctact gcaggggcc    60
gtgtccatgg gcttttgccg cagcgcgctg catccgctga gcctgctggt gcaggcgatt   120
atgctggcga tgaccctggc gctgggcacc ctgccggcgt ttctgccgtg cgaactgcag   180
ccgcatggcc tggtgaactg caactggctg ttttctgaaaa gcgtgccgca ttttagcatg   240
gcggcgccgc gcggcaacgt gaccagcctg agcctgagca gcaaccgcat tcatcatctg   300
catgatagcg atttttgcgca tctgccgagc ctgcgccatc tgaacctgaa atggaactgc   360
ccgcggtgg gcctgagccc gatgcatttt ccgtgccata tgaccattga accgagcacc   420
tttctggcg tgccgaccct ggaagaactg aacctgagct ataacaacat tatgaccgtg   480
ccggcgctgc cgaaaagcct gattagcctg agcctgaacat ataccaacat tctgatgctg   540
gatagcgcga gcctggcggg cctgcatgcg ctgcgctttc tgtttatgga tggcaactgc   600
tattataaaa acccgtgccg ccaggcgctg aagtggcgc cgggcgcgct gctgggcctg   660
ggcaacctga cccatctgag cctgaaatat aacaacctga ccgtggtgcc gcgcaacctg   720
ccgagcggc tggaatatct gctgctgagc tataaccgca ttgtgaaact gcgccgaa    780
gatctggcga acctgaccgc gctgcgcgtg ctggatgtgg gcggcaactg ccgccgctgc   840
gatcatgcg cgaaccgtg catggaatgc ccgcgccatt ttccgcagct gcatccggat   900
acctttagcc atctgagccg cctggaaggc ctggtgctga agatagcag cctgagctgg   960
ctgaacgcga gctggtttcg cggcctgggc aacctgcgcg tgctggatct gagcgaaaac  1020
tttctgtata aatgcattac caaaaaccaaa gcgtttcagg gcctgaccca gctgcgcaaa  1080
ctgaacctga gctttaacta tcagaaacgc gtgagctttg cgcatctgag cctggcgccg  1140
agctttggca gcctggtggc gctgaaagaa ctggatatgc atggcatttt ttttcgcagc  1200
ctggatgaaa ccaccctgcg cccgcgtggcg cgcctgccga tgctgcagac cctgcgcctg  1260
cagatgaact ttattaacca ggcgcagctg gcattttttc gcgcgtttcc gggcctgcgc  1320
tatgtggatc tgagcgataa ccgcattagc ggcgcgagcg aactgaccgc gaccatgggc  1380
gaagcggatg cggcgaaaa agtgtggctg cagccgggcg atctggcgcc ggcgccggtg  1440
gataccccga gcagcgaaga ttttcgcccg aactgcgaca cctgaactt taccctggat  1500
ctgagccgca acaacctggt gaccgtgcag ccggaaatgt tgcgcagct gagccatctg  1560
cagtgcctgc gcctgagcca taactgcatt agccaggcgg tgaacggcag ccagtttctg  1620
ccgctgaccg gcctgcaggt gctggatctg agccataaca aactggatct gtatcatgaa  1680
catagcttta ccgaactgcc gcgcctggaa gcgctgatc tgagcctataa cagcagcga  1740
tttggcatgc agggcgtggg ccataacttt agctttgtgg cgcatctgcg caccctgcgc  1800
catctgagcc tggcgcataa caacattcat agccaggtga ccagcagct gtgcagcacc  1860
agcctgcgcg cgctggattt tagcggcaac gcgctgggcc atatgtgggc ggaaggcgat  1920
ctgtatctgc atttttttca gggcctgagc ggcctgattt ggctggatct gagccagaac  1980
cgcctgcata ccctgctgcc gcagacccct cgcaacctgc cgaaaagcct gcaggtgctg  2040
cgcctgcgcg ataactatct ggcgtttttt aaatggtgga gcctgcattt tctgccgaaa  2100
ctggaagtgc tggatctggc gggcaaccag ctgaaagcgc tgaccaacgg cagcctgccg  2160
gcgggcaccc gcctgcgccg cctggatgtg agctgcaaca gcattagctt tgtggcgccg  2220
ggcttttta gcaaagcgaa agaactgcgc gaactgctga tgagcgcgaa cgcgctgaaa  2280
accgtggatc atagctggtt tggcccgctg gcgagcgcgc tgcagattct ggatgtgagc  2340
gcgaacccgc tgcattgcgc gtgcggcgcg cgtttatgg attttctgct ggaagtgcag  2400
gcggcggtgc cgggcctgcc gagccgcgtg aaatgcggca gccgggcca gctgcagggc  2460
ctgagcattt ttgcgcagga tctgcgctg tgcctggatg aagcgctgac ctgggattgc  2520
tttgcgctga gcctgctggc ggtggcgctg gcctgggcg tgccgatgct gcatcatctg  2580
tgcggctggg atctgtggta ttgctttcat ctgtgcctgg cgtggctgcc gtggcgcggc  2640
cgccagagcg gccgcgatga agatgcgctg ccgtatgatg cgtttgtggt gtttgataaa  2700
acccgaggcg cggttggcgga ttgggtgtat aacgaactgc gcggccagct ggaagaattgc  2760
cgcggccgct gggcgctgcg cctgtgcctg gaagaacgcg attggctgcc gggcaaaacc  2820
ctgtttgaaa acctgtgggc gagcgtgtat ggcagccgca aaaccctgtt tgtgctggcg  2880
cataccgatc gcgtgagcgg cctgctgcgc gcgagctttc tgctggcga gcagcgcctg  2940
ctggaagatc gcaaaagatgt ggtggtgctg gtgattctga gccgatggg ccgccgcagc  3000
cgctatgtgc gcctgcgcca gcgcctgtgc cgcagagcg tgctgctgtg gccgcatcag  3060
ccgagcggcc agcgcagctt tgggcgcag ctgggcatgg cgctgacccg cgataaccat  3120
cattttata accgcaactt tgccagggc ccgaccgcgg aagggcggat caggcggatc  3180
acccaaatct tgtgacaaaa ctcacacatg cccaccgtgc ccagcactg aactcctggg  3240
gggaccgtca gtcttcctct tcccccaaa acccaaggac accctcatga tctcccgag  3300
ccctgaggtc acatgcgtgg tggtggacgt gagccacgaa gaccctgagg tcaagttcaa  3360
ctggtacgtg gacggcgtgg aggtgcataa tgccaagaca aagccgcggg aggagcagta  3420
caacagcacg taccgtgtgg tcagcgtcct caccgtcctg caccaggact ggctgaatgg  3480
caaggagtac aagtgcaagg tctccaacaa agccctccca gcccccatcg agaaaaccat  3540
ctccaaagcc aaagggcagc cccgagaacc acaggtgtac accctgcccc catcccggga  3600
ggagatgacc aagaaccagg tcagcctgac ctgcctggtc aaaggcttct atcccagcga  3660
catcgccgtg gagtgggaga gcaatgggca gccggagaac aactacaaga ccacgcctcc  3720
cgtgctggac tccgacggct ccttcttcct ctacagcaag ctcaccgtgg acaagagcag  3780
gtggcagcag gggaacgtct tctcatgctc cgtgatgcat gaggctctgc acaaccacta  3840
cacgcagaag agcctctccc tgtctccggg taaatag                         3877
```

| SEQ ID NO: 5 | moltype = DNA length = 1503 |
|---|---|
| FEATURE | Location/Qualifiers |
| source | 1..1503 |
| | mol_type = other DNA |
| | organism = synthetic construct |

SEQUENCE: 5

```
atgaggggca tgaagctgct gggggcgctg ctggcactgg cggccctact gcaggggcc    60
gtgtccatga gcatgctgtt ttatccctg attaccgcgt ttctgattgg cattcaggcg   120
```

```
gaaccgcata gcgaaagcaa cgtgccggcg ggccatacca ttccgcaggc gcattggacc    180
aaactgcagc atagcctgga taccgcgctg cgccgcgcgc gcagcgcgcc ggcggcggcg    240
attgcgcgc gcgtggcggg ccagaccgc aacattaccg tggatccgcg cctgtttaaa     300
aaacgccgc tgcgcagccc gcgcgtgctg tttagcaccc agccgccgcg cgaagcggcc    360
gatacccagg atctggattt tgaagtgggc ggcgcggcgc cgtttaaccg cacccatgcc   420
agcaaacgca gcagcagcca tccgattttt catcgcggcg aatttagcgt gtgcgatagc   480
gtgagcgtgt gggtgggcga taaaaccacc gcgaccgata ttaaaggcaa agaagtgatg   540
gtgctgggca agtgaacat taacaacagc gtgtttaaac agtattttt tgaaaccaaa    600
tgccgcgatc cgaacccggt ggatagcggc tgccgcggca ttgatagcaa acattggaac   660
agctattgca ccaccaccca tacctttgtg aaagcgctga ccatgatgg caaacaggcg   720
gcgtggcgct ttattcgcat tgataccgcg tgcgtgtgcg tgctgagccg caaagcggtg   780
cgccgcgcgg gcggatcagg cggatcaccc aaatcttgtg acaaaactca cacatgccca   840
ccgtgcccag cacctgaact cctggggga ccgtcagtct tcctcttccc cccaaaaccc    900
aaggacaccc tcatgatctc ccggacccct gaggtcacat gcgtggtggt ggacgtgagc   960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag ggcagccccg agaaccacag   1200
gtgtacaccc tgcccccatc ccgggaggag atgaccaaga accaggtcag cctgacctgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaaa   1500
tag                                                                 1503

SEQ ID NO: 6           moltype = DNA   length = 1111
FEATURE                Location/Qualifiers
source                 1..1111
                       mol_type = other DNA
                       organism = synthetic construct
SEQUENCE: 6
atgaggggca tgaagctgct ggggggcgctg ctggcactgg cggccctact gcaggggggcc   60
gtgtccatgc gcctgtggat gcgcctgctg ccgctgctgg cgctgctggc gctgtggggc    120
ccggatccgg cggcggcgtt tgtgaaccag catctgtgcg gcagccatct ggtggaagcg   180
ctgtatctgg tgtgcggcga acgcggcttt ttttatacc cgaaaacccg ccgcgaagcg   240
gaagatctgc aggtgggcca ggtggaactg ggcgcggcc cgggcgcggg cagcctgcag   300
ccgctggcgc tggaaggcag cctgcagaaa cgcggcattg tggaacagtg ctgcaccagc   360
atttgcagcc tgtatcagct ggaaaactat tgcaacgggc ggatcaggcg gatcacccaa   420
atcttgtgac aaaactcaca catgcccacc gtgcccagca cctgaactcc tgggggggacc    480
gtcagtcttc ctcttccccc caaaacccaa ggacaccctc atgatctccc ggaccccctga   540
ggtcacatgc gtggtggtgg acgtgagcca cgaagaccct gaggtcaagt tcaactggta   600
cgtggacggc gtggaggtgc ataatgccaa gacaaagccg cgggaggagc agtacaacag   660
cacgtaccgt gtggtcagcg tcctcaccgt cctgcaccag gactggctga atggcaagga   720
gtacaagtgc aaggtctcca acaaagcct cccagccccc atcgagaaaa ccatctccaa     780
agccaaaggg cagccccgag aaccacaggt gtacaccctg cccccatccc gggaggagat   840
gaccaagaac caggtcagcc tgacctgcct ggtcaaaggc ttctatccca gcgacatcgc   900
cgtggagtgg gagagcaatg ggcagccgga gaacaactac aagaccacgc ctcccgtgct   960
ggactccgac ggctccttct tcctctacag caagctcacc gtggacaaga gcaggtggca   1020
gcaggggaac gtcttctcat gctccgtgat gcatgaggct ctgcacaacc actacacgca   1080
gaagagcctc tccctgtctc cgggtaaata g                                   1111

SEQ ID NO: 7           moltype = DNA   length = 7421
FEATURE                Location/Qualifiers
source                 1..7421
                       mol_type = other DNA
                       organism = synthetic construct
SEQUENCE: 7
ttctagaata atcaacctct ggattacaaa atttgtgaaa gattgactgg tattcttaac    60
tatgttgctc cttttacgct atgtggatac gctgctttaa tgcctttgta tcatgctatt   120
gcttcccgta tggctttcat tttctcctcc ttgtataaat cctggttgct gtctctttat    180
gaggagttgt ggcccgttgt caggcaacgt ggcgtggtgt gcactgtgtt tgctgacgca    240
accccactg gttgggggcat tgccaccacc tgtcagctcc tttccgggac tttcgctttc      300
cccctcccta ttgccacggc ggaactcatc gccgcctgcc ttgcccgctg ctggacaggg    360
gctcggctgt tgggcactga caattccgtg gtgttgtcgg ggaaatcatc gtcctttcct   420
tggctgctcg cctgtgttgc cacctggatt ctgcgcggga cgtccttctg ctacgtccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga ggccgggcga ccaaaggtcg   900
cccgacgccc gggctttgcc cggcggcct cagtgagcga gcgagcgcgc agctggcgt     960
aatgccaag aggcccgcac cgatcgccct tcccaacagt tgcgcagcct gaatggcgaa    1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aaagaagtat tgcgacaacg gttaatttgc   1200
gtgatggaca gactcttta ctcggtgcct cactgatta taaaaacact tctcaggatt     1260
ctggcgtacc gttcctgtct aaaatccctt taatcggcct cctgtttagc tcccgctctg   1320
```

```
attctaacga ggaaagcacg ttatacgtgc tcgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttccccgtc aagctctaaa tcgggggctc cctttagggt tccgatttag tgctttacgg   1560
cacctcgacc ccaaaaaact tgattagggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtcattctt ttgatttata agggattttg   1740
ccgatttcgg cctattggtt aaaaaatgag ctgatttaac aaaaatttaa cgcgaatttt   1800
aacaaaatat taacgtttac aatttaaata tttgcttata caatcttcct gtttttgggg   1860
cttttctgat tatcaaccgg ggtacatatg attgacatgc tagttttacg attaccgttc   1920
atcgattctc ttgtttgctc cagactctca ggcaatgacc tgatagcctt tgtagagacc   1980
tctcaaaaat agctaccctc tccggcatga atttatcagc tagaacggtt gaatatcata   2040
ttgatggtga tttgactgtc tccggccttt ctcacccgtt tgaatcttta cctacacatt   2100
actcaggcat tgcatttaaa atatatgagg gttctaaaaa tttttatcct tgcgttgaaa   2160
taaaggcttc tcccgcaaaa gtattacagg gtcataatgt ttttggtaca accgatttag   2220
ctttatgctc tgaggcttta ttgcttaatt ttgctaattc tttgccttgc ctgtatgatt   2280
tattggatgt tggaattcct gatgcggtat tttctcctta cgcatctgtg cggtatttca   2340
caccgcatat ggtgcactct cagtacaatc tgctctgatg ccgcatagtt aagccagccc   2400
cgacacccgc caacacccgc tgacgcgccc tgacgggctt gtctgctccc ggcatccgct   2460
tacagacaag ctgtgaccgt ctccgggagc tgcatgtgtc agaggttttc accgtcatca   2520
ccgaaacgcg cgagacgaaa gggcctcgtg atacgcctat ttttataggt taatgtcatg   2580
ataataatgg tttcttagac gtcaggtggc acttttcggg gaaatgtgcg cggaacccct   2640
atttgtttat ttttctaaat acattcaaat atgtatccgc tcatgagaca ataaccctga   2700
taaatgcttc aataatattg aaaaaggaag agtatgagta ttcaacattt ccgtgtcgcc   2760
cttattcct ttttttgcggc attttgcctt cctgtttttg ctcacccaga aacgctggtg   2820
aaagtaaaag atgctgaaga tcagttgggt gcacgagtgg gttacatcga actggatctc   2880
aacagcggta agatccttga gttttcgc cccgaagaac gttttccaat gatgagcact   2940
tttaaagttc tgctatgtgg cgcggtatta tcccgtattg acgccgggca agagcaactc   3000
ggtcgccgca tacactattc tcagaatgac ttggttgagt actcaccagt cacagaaaag   3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc   3300
aaactattaa ctggcgaact acttactcta gcttcccggc aacaattaat agactggatg   3360
gaggcggata aagttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggg gcctcactga ttaagcattg gtaactgtca   3600
gaccaagttt actcatatat actttagatt gatttaaaac ttcattttta atttaaaagg   3660
atctaggtga agatcctttt tgataatctc atgaccaaaa tcccttaacg tgagttttcg   3720
ttccactgag cgtcagaccc cgtagaaaag atcaaaggat cttcttgaga tcctttttt   3780
ctgcgcgtaa tctgctgctt gcaaacaaaa aaaccaccgc taccagcggt ggtttgtttg   3840
ccggatcaag agctaccaac tctttttccg aaggtaactg gcttcagcag agcgcagata   3900
ccaaatactg tccttctagt gtagccgtag ttaggccacc acttcaagaa ctctgtagca   3960
ccgcctacat acctcgctct gctaatcctg ttaccagtgg ctgctgccag tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc agggggaaac   4260
gcctggtatc tttatagtcc tgtcgggttt cgccacctct gacttgagcg tcgatttttg   4320
tgatgctcgt caggggggcg gagccatatgg aaaaacgcca gcaacgcggc cttttacgg   4380
ttcctggcct tttgctggcc ttttgctcac atgttctttc ctgcgttatc ccctgattct   4440
gtggataacc gtattaccgc ctttgagtga gctgataccg ctcgccgcag ccgaacgacc   4500
gagcgcagcg agtcagtgag cgaggaagcg gaagagcgcc caatacgcaa accgcctctc   4560
cccgcgcgtt ggccgattca ttaatgcagc agctgcgcgc tcgctcgctc actgaggccg   4620
cccgggcaaa gcccgggcgt cgggcgacct ttggtcgccc ggcctcagtg agcgagcgag   4680
cgcgcagaga gggagtggcc aactccatca ctagggtgtc cttgtagtta atgattaacc   4740
cgccatgcta cttatctacg tagccatgct ctaggacatt gattattgac tagtggagtt   4800
ccgcgttaca taacttacgg taaatggccc gcctggctga acatgcca accccccgcc   4860
attgacgtca ataatgacgt atgttcccat agtaacgcca ataggggactt tccattacg   4920
tcaatgggtg gagtatttac ggtaaactgc ccacttggca gtacatcaag tgtatcatat   4980
gccaagtacg cccctattg acgtcaatga cggtaaatgg cccgcctggc attatgccca   5040
gtacatgacc ttatgggact ttcctacttg gcagtacatc tacgtattag tcatcgctat   5100
taccatggtc gaggtgagcc ccacgttctg cttcactctc cccatctccc cccccctccc   5160
acccccaatt ttgtatttat ttattttta attatttgt gcagcgatgg gggcgggggg   5220
ggggggggc gcgcgccagg cggggcgggg cgggggcgagg ggcggggcgg ggcggaggcgg   5280
agaggtgcgc cggcagccaa tcagagcggc gcgctccgaa agtttccttt tatggcgagg   5340
cggcggcggc ggcggcccta taaaagcga agcgcgcggc gggcgggagt cgctcgcgc   5400
tgccttcgcc ccgtgccccg ccctcgccgc cgcctcgcgc cgcccgcccg gctctgactg   5460
accgcgttac taaaacaggt aagtccggcc tccgcgccgg gttttggcgc ctcccgcggg   5520
cgcccccctc ctcacggcga gcgctgccac gtcagacgaa gggcgcagcg agcgtcctga   5580
tccttccgcc cggacgctca ggacagcggc ccgctgctca taagactcgg ccttagaacc   5640
ccagtatcag cagaaggaca ttttaggacg ggacttgggt gactctaggg cactggtttt   5700
ctttccagag agcggaacag gcgaggaaaa gtagtccctt ctcggcgatt ctgcggaggg   5760
atctccgtgg ggcggtgaac gccgatgatg cctctactaa ccatgttcat gttttctttt   5820
tttttctaca gtcctgggt gacaacagg gtaccgccac catgagggc atgaagctgc   5880
tgggggcgct gctggcactg gcggccctac tgcaggggg cgtgtccctg aagatcgcag   5940
ccttcaacat ccagacattt ggggagacca agatgtccaa tgccaccctc gtcagctaca   6000
ttgtgcagat cctgagccgc tatgacatcg ccctggtcca ggaggtcaga gacagccacc   6060
```

```
tgactgccgt ggggaagctg ctggacaacc tcaatcagga tgcaccagac acctatcact  6120
acgtggtcag tgagccactg ggacggaaca gctataagga gcgctacctg ttcgtgtaca  6180
ggcctgacca ggtgtctgcg gtggacagct actactacga tgatggctgc gagccctgcg  6240
ggaacgacac cttcaaccga gagccagcca ttgtcaggtt cttctcccgg ttcacagagg  6300
tcagggagtt tgccattgtt cccctgcatg cggccccggg ggacgcagta gccgagatcg  6360
acgctctcta tgacgtctac ctggatgtcc aagagaaatg gggcttggag gacgtcatgt  6420
tgatgggcga cttcaatgcg ggctgcagct atgtgagacc ctcccagtgg tcatccatcc  6480
gcctgtggac aagccccacc ttccagtggc tgatccccga cagcgctgac accacagcta  6540
cacccacgca ctgtgcctat gacaggatcg tggttgcagg gatgctgctc cgaggcgcac  6600
ttgttcccga ctccggctct cccttttaact tccaggctgc ctatggcctg agtgaccaac  6660
tggcccaagc catcagtgac cactatccag tggaggtgat gctgaagggc ggatcaggcg  6720
gatcacccaa atcttgtgac aaaactcaca catgcccacc gtgcccagca cctgaactcc  6780
tggggggacc gtcagtcttc ctcttccccc caaaacccaa ggacaccctc atgatctccc  6840
ggacccctga ggtcacatgc gtggtggtgg acgtgagcca cgaagacccct gaggtcaagt  6900
tcaactggta cgtggacggc gtggaggtgc ataatgccaa gacaaagccg cgggaggagc  6960
agtacaacag cacgtaccgt gtggtcagcg tcctcaccgt cctgcaccag gactggctga  7020
atggcaagga gtacaagtgc aaggtctcca acaaagcccc cccagccccc atcgagaaaa  7080
ccatctccaa agccaaaggg cagccccgag aaccacaggt gtacaccctg cccccatccc  7140
gggaggagat gaccaagaac caggtcagcc tgacctgcct ggtcaaaggc ttctatccca  7200
gcgacatcgc cgtggagtgg gagagcaatg ggcagccgga gaacaactac aagaccacgc  7260
ctcccgtgct ggactccgac ggctccttct tcctctacag caagctcacc gtggacaaga  7320
gcaggtggca gcagggggaac gtcttctcat gctccgtgat gcatgaggct ctgcacaacc  7380
actacacgca gaagagcctc tccctgtctc cgggtaaata g                      7421

SEQ ID NO: 8              moltype = DNA  length = 9284
FEATURE                   Location/Qualifiers
source                    1..9284
                          mol_type = other DNA
                          organism = synthetic construct
SEQUENCE: 8
ttctagaata atcaacctct ggattacaaa atttgtgaaa gattgactgg tattcttaac  60
tatgttgctc cttttacgct atgtggatac gctgctttaa tgcctttgta tcatgctatt  120
gcttcccgta tggctttcat tttctcctcc ttgtataaat cctggttgct gtctctttat  180
gaggagttgt ggcccgttgt caggcaacgt ggcgtggtgt gcactgtgtt tgctgacgca  240
acccccactg gttgggcat tgccaccacc tgtcagctcc tttccgggac tttcgctttc  300
cccctcccta ttgccacggc ggaactcatc gccgctgcc ttgcccgctg ctggacaggg  360
gctcggctgt tgggcactga caattccgtg gtgttgtcgg ggaaatcatc gtcctttcct  420
tggctgctcg cctgtgttgc cacctggatt ctgcgcggga cgtccttctg ctacgtccct  480
tcggccctca atccagcgga ccttccttcc gcggcctgc tgccggctct gcggcctctt  540
ccgcgtcttc gccttcgccc tcagacgagt cggatctccc tttgggccgc ctccccgcct  600
aagcttatcg ataccgtcga gatctaactt gtttattgca gcttataatg gttacaaata  660
aagcaatagc atcacaaatt tcacaaataa agcattttt tcactgcatt ctagttgtgg  720
tttgtccaaa ctcatcaatg tatcttatca tgtctgtata acctctgatt agagcatgg  780
gctacgtaga taagtagcat ggcgggttaa tcattaacta caaggaaccc ctagtgatgg  840
agttggccac tccctctctg cgcgctcgct cgctcactga ggccgggcga ccaaaggtcg  900
cccgacgccc gggctttgcc cgggcggcct cagtgagcga gcgagcgcgc agctggcgt  960
aatagcgaag aggcccgcac cgatcgccct tcccaacagt tgcgcagcct gaatggcgaa  1020
tggaattcca gacgattgag cgtcaaaatg taggtatttc catgagcgtt tttcctgttg  1080
caatggctgg cggtaatatt gttctggata ttaccagcaa ggccgatagt ttgagttctt  1140
ctactcaggc aagtgatgtt attactaatc aaagaagtat tgcgacaacg gttaatttgc  1200
gtgatgaaca gactctttta ctcggtggcc tcactgatta taaaaacact tctcaggatt  1260
ctggcgtacc gttcctgtct aaaatccctt taatcggcct cctgtttagc tcccgctctg  1320
attctaacga ggaagcacg ttatacgtgt cgtcaaagc aaccatagta cgcgccctgt  1380
agcggcgcat taagcgcggc gggtgtggtg gttacgcgca gcgtgaccgc tacacttgcc  1440
agcgccctag cgcccgctcc tttcgctttc ttcccttcct ttctcgccac gttcgccggc  1500
tttccccgtc aagctctaaa tcgggggctc cctttagggt tccgatttag tgctttacgg  1560
cacctcgacc ccaaaaaact tgattagggt gatggttcac gtagtgggcc atcgccctga  1620
tagacggttt ttcgcccttt gacgttggag tccacgttct ttaatagtgg actcttgttc  1680
caaactggaa caacactcaa ccctatctcg gtctattctt tgatttata agggattttg  1740
ccgatttcgg cctattggtt aaaaaatgag ctgatttaac aaaaatttaa cgcgaatttt  1800
aacaaaatat taacgtttac aatttaaata tttgcttata caatcttcct gttttgggg  1860
cttttctgat tatcaaccgg ggtacatatg attgacatgc tagttttacg attaccgttc  1920
atcgattctc ttgtttgctc cagactctca ggcaatgacc tgatagcctt tgtagagacc  1980
tctcaaaaat agctaccctc tccggcatga atttatcagc taagaacggtt gaatatcata  2040
ttgatggtga tttgactgtc tccggccttt ctcacccgtt tgaatcttta cctacacatt  2100
actcaggcat tgcatttaaa atatatgagg gttctaaaaa tttttatcct tgcgttgaaa  2160
taaaggcttc tcccgcaaaa gtattacagg tcataatgt ttttggtaca accgatttag  2220
ctttatgctc tgaggcttta ttgcttaatt tttgccttgc ctgtatgatt  2280
tattgattgt tggaattcct gatgcggtat tttctcctta cgcatctgtg cggtatttca  2340
caccgcatat ggtgcactct cagtacaatc tgctctgatg ccgcatagtt aagccagccc  2400
cgacacccgc caacacccgc tgacgcgccc tgacgggctt gtctgctccc ggcatccgct  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaaccct  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct ttttttgcggc attttgcctt cctgtttttg ctcacccaga aacgctggtg  2820
aaagtaaaag atgctgaaga tcagttgggt gcacgagtgg gttacatcga actggatctc  2880
aacagcggta agatccttga gagttttcgc cccgaagaac gttttccaat gatgagcact  2940
```

```
tttaaagttc tgctatgtgg cgcggtatta tcccgtattg acgccgggca agagcaactc 3000
ggtcgccgca tacactattc tcagaatgac ttggttgagt actcaccagt cacagaaaag 3060
catcttacgg atggcatgac agtaagagaa ttatgcagtg ctgccataac catgagtgat 3120
aacactgccg ccaacttact tctgacaacg atcggaggac cgaaggagct aaccgctttt 3180
ttgcacaaca tggggatca tgtaactcgc cttgatcgtt gggaaccgga gctgaatgaa 3240
gccataccaa acgacgagcg tgacaccacg atgcctgtag caatggcaac aacgttgcgc 3300
aaactattaa ctggcgaact acttactcta gcttcccggc aacaattaat agactggatg 3360
gaggcggata aagttgcagg accacttctg cgctcggccc ttccggctgg ctggtttatt 3420
gctgataaat ctggagccgg tgagcgtggg tctcgcggta tcattgcagc actggggcca 3480
gatggtaagc cctcccgtat cgtagttatc tacacgacgg ggagtcaggc aactatggat 3540
gaacgaaata gacagatcgc tgagataggt gcctcactga ttaagcattg gtaactgtca 3600
gaccaagttt actcatatat actttagatt gatttaaaac ttcattttta atttaaaagg 3660
atctaggtga agatccttt tgataatctc atgaccaaaa tcccttaacg tgagttttcg 3720
ttccactgag cgtcagaccc cgtagaaaag atcaaaggat cttcttgaga tcctttttt 3780
ctgcgcgtaa tctgctgctt gcaaacaaaa aaaccaccgc taccagcggt ggtttgtttg 3840
ccggatcaag agctaccaac tcttttccg aaggtaactg gcttcagcag agcgcagata 3900
ccaaatactg tccttctagt gtagccgtag ttaggccacc acttcaagaa ctctgtagca 3960
ccgcctacat acctcgctct gctaatcctg ttaccagtgg ctgctgccag tggcgataag 4020
tcgtgtctta ccgggttgga ctcaagacga tagttaccgg ataaggcgca gcggtcgggc 4080
tgaacggggg gttcgtgcac acagcccagc ttggagcgaa cgacctacac cgaactgaga 4140
tacctacagc gtgagctatg agaaagcgcc acgcttcccg aagggagaaa ggcggacagg 4200
tatccggtaa gcggcagggt cggaacagga gagcgcacga gggagcttcc agggggaaac 4260
gcctggtatc tttatagtcc tgtcgggttt cgccacctct gacttgagcg tcgatttttg 4320
tgatgctcgt caggggggcg gagcctatgg aaaaacgcca gcaacgcggc cttttttacgg 4380
ttcctggcct tttgctggcc ttttgctcac atgttctttc ctgcgttatc ccctgattct 4440
gtggataacc gtattaccgc cttttgagtga gctgataccg ctcgccgcag ccgaacgacc 4500
gagcgcagcg agtcagtgag cgaggaagcg gaagagcgcc caatacgcaa accgcctctc 4560
cccgcgcgtt ggccgattca ttaatgcagc agctgcgcgc tcgctcgctc actgaggccg 4620
cccgggcaaa gcccgggcgt cgggcgacct ttggtcgccc ggcctcagtg agcgagcgag 4680
cgcgcagaga gggagtggcc aactccatca ctagggggttc cttgtagtta atgattaacc 4740
cgccatgcta cttatctacg tagccatgct ctaggacatt gattattgac tagtggagtt 4800
ccgcgttaca taacttacgg taaatggccc gcctggctga ccgcccaacg acccccgccc 4860
attgacgtca ataatgacgt atgttccat agtaacgcca atagggactt tccattgacg 4920
tcaatgggtg gagtatttac ggtaaactgc ccacttggca gtacatcaag tgtatcatat 4980
gccaagtacg cccctattg acgtcaatga cggtaaatgg cccgcctggc attatgccca 5040
gtacatgacc ttatgggact ttcctacttg gcagtacatc tacgtattag tcatcgctat 5100
taccatggtc gaggtgagcc ccacgttctg cttcactctc cccatctccc cccctcccc 5160
accccaatt ttgtatttat ttattttta attatttttgt gcagcgatgg gggcgggggg 5220
gggggggggc gcgcgccagg cggggcgggg cggggcgagg ggcggggcgg gcgaggcggg 5280
agaggtgcgg cggcagccaa tcagagcggc gcgctccgaa agtttccttt tatggcgagg 5340
cggcggcggc ggcggcccta taaaaagcga agcgcgcggc gggcgggagt cgctgcgcgc 5400
tgccttcgcc ccgtgcccg ctccgccgcc gcctcgcgcc gcccgccccg gctctgactg 5460
accgcgttac taaaacaggt aagtccggcc tccgcgccgg gttttggcgc ctcccgcggg 5520
cgcccccctc ctcacggcga gcgctgccac gtcagacgaa gggcgcagcg agcgtcctga 5580
tccttccgcc cggacgctca ggacagcggc ccgctgctca taagactcgg ccttagaacc 5640
ccagtatcag cagaaggaca ttttaggacg ggacttgggt gactctaggg cactggtttt 5700
ctttccagag agcggaacag gcgaggaaaa gtagtccctt ctcggcgatt ctgcggaggg 5760
atctccgtgg ggcggtgaac gccgatgatg cctctactaa ccatgttcat gttttctttt 5820
tttttctaca ggtcctgggt gacgaacagg gtaccgccac cgccagaccc tgccgtgcat 5880
ttattttggg ggcggcctgc tgccgtttgg catgctgtgc gcgagcagca ccaccaaatg 5940
caccgtggca catgaagtgg cggattgcag ccatctgaaa ctgacccagg tgccgggaga 6000
tctgccgacc aacattaccg tgctgaacct gacccataac cagctgcgcc gcctgccggc 6060
ggcgaacttt accgctata gccagctgac cagcctggat gtgggcttta acaccattag 6120
caaactggaa ccggaactgt gccagaaact gccgatgctg aaagtgctga acctgcagca 6180
taacgaactg agccagctga gcgataaaac ctttgcgttt tgcaccaacc tgaccgaact 6240
gcatctgatg agcaacagca ttcagaaaat taaaaacaac ccgtttgtga aacagaaaaa 6300
cctgattacc ctggatctga gccataacgg cctgagcagc accaaactgg gcacccaggt 6360
gcagctggaa aacctgcagg aactgctgct gagcaacaac aaaattcagg cgctgaaaag 6420
cgaagaactg gatattttg cgaacagcag cctgaaaaaa ctggaactga gcagcaacca 6480
gattaaagaa tttagcccgg gctgctttca tgcgattggc cgcctgtttg gcctgttttct 6540
gaacaacgtg cagctgggcc cgagcctgac cgaaaaactg tgcctggaac tggcgaacac 6600
cagcattcgc aacctgagcc tgagcaacag ccagctgagc accaccagca caccacctt 6660
tctgggcctg aaatgaccaa acctgaccat gctggatctg agctataaca acctgaacgt 6720
ggtgggcaac gatagctttc cgtggctgcc gcagctggaa tattttttc tggaatataa 6780
caacattcag catctgttta gccatagcct gcatgccctg tttaacgtgc gctatctgaa 6840
cctgaaacgc agctttacca aacagagcat tagcctggcg agcctgccga aaattgatga 6900
ttttagcttt cagtggctga aatgcctgga acatctgaac atggaagata cgatattccc 6960
gggcattaaa agcaacatgt ttaccggcct gattaacctg aaatatctga gctgagcaa 7020
cagctttacc agcctgcgca ccctgaccaa cgaaacctttt gtgagcctgg cgcatagccc 7080
gctgcatatt ctgaacctga ccaaaaacaa aattagcaaa attgaaagcg atgcgtttag 7140
ctggctgggc catctggaag tgctggatct gggcctgaac gaaattggcc aggaactgac 7200
cggccaggaa tggcgcggcc tggaaaacat ttttgaaatt tatctgagct ataacaaata 7260
tctgcagctg acccgcaaca gctttgcgct ggtgccgagc ctgcagcgcc tgatgctgcg 7320
ccgcgtggc ctgaaaaacg tggatagcag ccgggaccgc tttcagcgcc tgcgcaacct 7380
gaccattctg gatctgagca caacaacat tgcgaacatt aacgatgata tgctgaaggg 7440
cctggaaaaa ctgaaattc tggatctgca gcataacaac ctggcgcgcc tgtgaaaca 7500
tgcgaaccg gcggccgca tttatttct gaaaggcctg agccatcgc atattctgaa 7560
cctgaaagc aacggctttg atgaaattcc ggtggaagtg tttaaagatc tgtttgaact 7620
gaaaattatt gatctgggcc tgaacaacct gaacacccgt ccggcgagcg tgtttaacaa 7680
```

```
ccaggtgagc ctgaaaagcc tgaacctgca gaaaaacctg attaccagcg tggaaaaaaa   7740
agtgtttggc ccggcgtttc gcaacctgac cgaactggat atgcgcttta acccgtttga   7800
ttgcacctgc gaaagcattg cgtggtttgt gaactggatt aacgaaaccc ataccaacat   7860
tccggaactg agcagccatt atctgtgcaa caccccgccg cattatcatg ctttccggtt   7920
gcgcctgttt gataccagca gctgcaaaga tagcgcgcct tttgaactgt tttttatgat   7980
taacaccagc attctgctga ttttatttt tattgtgctg ctgattcatt ttgaaggctg   8040
gcgcattagc tttattgga acgtgagcgt gcatcgcgtg ctgggcttta agaaaattga   8100
tcgccagacc gaacagtttg aatatgcggc gtatattatt catgcgtata agataaaga   8160
ttgggtgtgg gaacattta gcagcatgga aaaagaagat cagagcctga aatttgcct   8220
ggaagaacgc gattttgaag cgggcgtgtt tgaactggaa gcgattgtga acagcattaa   8280
acgcagccgc aaaattattt ttgtgattac ccatcatctg ctgaaagatc cgctgtgcaa   8340
acgctttaaa gtgcatcatg cggtgcagca ggcgattgaa cagaacctgg atagcattat   8400
tctggtgttt ctggaagaaa ttccggatta taaactgaac catgcgctgt gcctgcgccg   8460
cggcatgtttt aaaagccatt gcattctgaa ctggccggtg cagaaagaac gcattgataa   8520
gtttcgccat aaactgcagg tggcgctggg cagcaaaaac agcgtgcatg gcggatcag   8580
gcggatcacc caaatcttgt gacaaaactc acacatgccc accgtgccca gcacctgaac   8640
tcctgggggg accgtcagtc ttcctcttcc ccccaaaacc caaggacacc ctcatgatct   8700
cccggacccc tgaggtcaca tgcgtggtgg tggacgtgag ccacgaagac cctgaggtca   8760
agttcaactg gtacgtggac ggcgtggagg tgcataatgc caagacaaag ccgcgggagg   8820
agcagtacaa cagcacgtac cgtgtggtca gcgtcctcac cgtcctgcac caggactggc   8880
tgaatggcaa ggagtacaag tgcaaggtct ccaacaaagc cctcccagcc cccatcgaga   8940
aaaccatctc caaagccaaa gggcagcccc gagaaccaca ggtgtacacc ctgccccat   9000
cccgggagga tgaccaag aaccaggtca gcctgacctg cctggtcaaa ggcttctatc   9060
ccagcgacat cgccgtggag tgggagagca atgggcagcc ggagaacaac tacaagacca   9120
cgcctcccgt gctggactcc gacggctcct tcttcctcta cagcaagctc accgtggaca   9180
agagcaggtg gcagcagggg aacgtcttct catgctccgt gatgcatgag gctctgcaca   9240
accactacac gcagaagagc ctctccctgt ctccgggtaa atag                    9284
```

SEQ ID NO: 9        moltype = DNA  length = 9738
FEATURE              Location/Qualifiers
source               1..9738
                      mol_type = other DNA
                      organism = synthetic construct
SEQUENCE: 9

```
ttctagaata atcaacctct ggattacaaa atttgtgaaa gattgactgg tattcttaac     60
tatgttgctc cttttacgct atgtggatac gctgctttaa tgcctttgta tcatgctatt    120
gcttcccgta tggctttcat tttctcctcc ttgtataaat cctggttgct gtctctttat    180
gaggagttgt ggcccgttgt caggcaacgt ggcgtggtgt gcactgtgtt tgctgacgca    240
accccactg gttggggcat tgccaccacc tgtcagctcc tttccgggac tttcgctttc    300
cccctcccta ttgccacggc ggaactcatc gccgcctgcc ttgcccgctg ctggacaggg    360
gctcggctgt tgggcactga caattccgtg gtgttgtcgg ggaaatcatc gtcctttcct    420
tggctgctcg cctgtgttgc cacctggatt ctgcgcggga cgtccttctg ctacgtccct    480
tcggccctca atccagcgga ccttccttcc cgcggcctgc tgccggctct gcgggcctct    540
ccgcgtcttc gccttcgccc tcagacgagt cggatctccc tttgggccgc ctccccgcct    600
aagcttatcg ataccgtcga gatcaactt gtttattgca gcttataatg gttacaaata    660
aagcaatagc atcacaaatt tcacaaataa agcatttttt tcactgcatt ctagttgtgg    720
tttgtccaaa ctcatcaatg tatcttatca tgtctggatc tcgactcga tagagcattg    780
gctacgtaga taagtagcat ggcgggttaa tcattaacta caaggaaccc ctagtgatgg    840
agttggccac tccctctctg cgcgctcgct cgctcactga ggccgggcga ccaaaggtcg    900
cccgacgccc gggctttgcc cgggcggcct cagtgagcga gcgagcgcgc cagctggcgt    960
aataccgaag aggcccgcac cgatcgccct cccaacagt tgcgcagcct gaatggcgaa   1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aaagaagtat tgcgacaacg gttaatttgc   1200
gtgatgaaca gactctttta ctcggtggcc tcactgatta taaaaaacact tctcaggatt   1260
ctggcgtacc gttcctgtct aaaatccctt aatcggcct cctgtttagc tcccgctctg   1320
attctaacga ggaaagcacg ttatacgtgt cgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttcccccgtc aagctctaaa tcggggggctc cctttagggt tccgatttag tgctttacgg   1560
cacctcgacc ccaaaaaact tgattagggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtctattctt ttgatttata agggattttg   1740
ccgatttcgg cctattggtt aaaaaatgag ctgatttaac aaaaatttaa cgcgaattt    1800
aacaaaatat taacgtttac aatttaaata tttgcttata caatcttcct gtttttgggg   1860
cttttctgat tatcaaccgg ggtacatatg attgacatgc tagttttacg attaccgttc   1920
atcgattctc ttgtttgctc cagactctca ggcaatgacc tgatagcctt gtagagacc   1980
tctcaaaaat agctaccctc tccggcatga atttatcagc taagacggtt gaatatcata   2040
ttgatggtga tttgactgtc tccggccttt ctcaccgt tgaatctta cctacacatt   2100
actcaggcat tgcatttaaa atatatgagg gttctaaaaa tttttatcct tgcgttgaaa   2160
taaaggcttc tcccgcaaaa gtattacagg gtcataatgt ttttggtaca accgatttag   2220
ctttatgctc tgaggcttta ttgcttaatt ttgctaattc tttgccttgc ctgtatgatt   2280
tattggatgt tggaattcct gatgcggtat tttcctta cgcatctgtg cggtatttca   2340
caccgcata ggtgcactct cagtacaatc tgctctgatg ccgcatagtt aagccagccc   2400
cgacaccccgc caacacccgc tgacgcgccc tgacgggctt gtctgctccc ggcatccgct   2460
tacagacaag ctgtgaccgt ctccgggagc tgcatgtgtc agaggttttc accgtcatca   2520
ccgaaacgcg cgagacgaaa gggcctcgtg atacgcctat ttttataggt taatgtcatg   2580
ataataatgg tttcttagac gtcaggtggc acttttcggg gaaatgtgcg cggaacccct   2640
atttgtttat ttttctaaat acattcaaat atgtatccgc tcatgagaca ataaccctga   2700
```

```
taaatgcttc aataatattg aaaaaggaag agtatgagta ttcaacattt ccgtgtcgcc   2760
cttattccct tttttgcggc attttgcctt cctgttttg ctcacccaga aacgctggtg    2820
aaagtaaaag atgctgaaga tcagttgggt gcacgagtgg gttacatcga actggatctc   2880
aacagcggta agatccttga gagttttcgc cccgaagaac gttttccaat gatgagcact   2940
tttaaagttc tgctatgtgg cgcggtatta tcccgtattg acgccgggca agagcaactc   3000
ggtcgccgca tacactattc tcagaatgac ttggttgagt actcaccagt cacagaaaag   3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc   3300
aaactattaa ctggcgaact acttactcta gcttcccggc aacaattaat agactggatg   3360
gaggcggata agttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggt gcctcactga ttaagcattg gtaactgtca   3600
gaccaagttt actcatatat actttagatt gatttaaaac ttcatttta atttaaaagg   3660
atctaggtga agatccttt tgataatctc atgaccaaaa tcccttaacg tgagttttcg   3720
ttccactgag cgtcagaccc cgtagaaaag atcaaaggat cttcttgaga tccttttttt   3780
ctgcgcgtaa tctgctgctt gcaaacaaaa aaaccaccgc taccagcggt ggtttgtttg   3840
ccggatcaag agctaccaac tctttttccg aaggtaactg gcttcagcag agcgcagata   3900
ccaaatactg tccttctagt gtagccgtag ttaggccacc acttcaagaa ctctgtagca   3960
ccgcctacat acctcgctct gctaatcctg ttaccagtgg ctgccgcaaa tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc agggggaaac   4260
gcctggtatc tttatagtcc tgtcgggttt cgccacctct gacttgagcg tcgatttttg   4320
tgatgctcgt cagggggggcg gagcctatgg aaaaacgcca gcaacgcggc ctttttacgg   4380
ttcctggcct tttgctggcc ttttgctcac atgttctttc ctgcgttatc ccctgattct   4440
gtggataacc gtattaccgc ctttgagtga gctgataccg ctcgccgcag ccgaacgacc   4500
gagcgcagcg agtcagtgag cgaggaagcg gaagagcgcc caatacgcaa accgcctctc   4560
cccgcgcgtt ggccgattca ttaatgcagc agctgcgcgc tcgctcgctc actgaggccg   4620
cccgggcaaa gcccgggcgt cgggcgacct ttggtcgccc ggcctcagtg agcgagcgag   4680
cgcgcagaga gggagtggcc aactccatca ctaggggttc cttgtagtta atgattaacc   4740
cgccatgcta cttatctacg tagccatgct ctaggacatt gattattgac tagtggagtt   4800
ccgcgttaca taacttacgg taaatggccc gcctggctga ccgcccaacg accccgccc    4860
attgacgtca ataatgacgt atgttccat agtaacgcca atagggactt tccattgacg    4920
tcaatggggtg gagtatttac ggtaaactgc ccacttggca gtacatcaag tgtatcatat   4980
gccaagtacg ccccctattg acgtcaatga cggtaaatgg cccgcctggc attatgccca   5040
gtacatgacc ttatgggact ttcctacttg gcagtacatc tacgtattag tcatcgctat   5100
taccatggtc gaggtgagcc ccacgttctg cttcactctc cccatctccc ccccctcccc   5160
accccccaatt ttgtatttat ttatttttta attatttttgt gcagcgatgg gggcgggggg   5220
ggggggggggc gcgcgccagg cggggcgggg cgggcgaggg gcggggcggg gcgaggcgg    5280
agaggtgcgg cggcagccaa tcagagcggc gcgctccgaa agtttccttt tatggcgagg   5340
cggcggcggc ggcggcccta taaaaagcga agcgcgcggc gggcgggagt cgctgcgcgc   5400
tgccttcgcc ccgtgcccg ctccgccgcc gcctcgcgcc gcccgcccg gctctgactg    5460
accgcgttac taaaacaggt aagtccggcc tccgcgccgg gttttggcgc ctcccgcggg   5520
cgccccctc ctcacggcga gcgctgccac gtcagacgaa gggcgcagcg agcgtcctga    5580
tccttccgcc cggacgctca ggacagcggc ccgctgctca taagactcgg ccttagaacc   5640
ccagtatcag cagaaggaca ttttaggacg ggacttgggt gactctaggg cactggtttt   5700
ctttccagag agcggaacag gcgaggaaaa gtagtccctt ctcggcgatt ctgcggaggg   5760
atctccgtgg ggcggtgaac gccgatgatg cctctactaa ccatgttcat gttttctttt   5820
tttttctaca ggtcctgggt gacgaacagg gtaccgccac catgaggggc atgaagctgc   5880
tgggggcgct gctggcactg gcggcctac tgcaggggc cgtgtccatg ggcttttgcc    5940
gcagcgcgct gcatccgctg agcctgctgg tgcaggcgat tatgctggcc atgaccctgg   6000
cgctgggcac cctgccggcg tttctgccgt gcgaactgca gccgcatggc ctggtgaact   6060
gcaactggct gtttctgaaa agcgtgccgc attttagcat ggcggcgccg cgcggcaacg   6120
tgaccagcct gagcctgagc agcaaccgca ttcatcatct gcatgatagc gattttgcgc   6180
atctgccgag cctgcgcgcat ctgaacctga ataggaactg ccgccggtg ggcctgcgcc   6240
cgatgcattt tccgtgccat atgaccattg aaccgagcac ctttctgcgt gtgccgacc    6300
tggaagaact gaacctgagc tataacaaca ttatgaccgt gccggcgctg ccgaaaagcc   6360
tgattagcct gagcctgagc cataccaaca ttctgatgct ggatagcgcg agcctggcgg   6420
gcctgcatgc gctgcgcttt ctgtttatgg atggcaactg ctattataaa aacccgtgcc   6480
gccaggcgcg ggaagtggcg ccgggcgcgc tgctggcgct gggcaacctg acccatctga   6540
gcctgaaata taacaacctg accggtgtgc cgcgcaacct gccgagcagc ctggaatatc   6600
tgctgctgag ctataaccgc attgtgaaac tggcgccgga agatctggcg aacctgaccg   6660
cgctgcgcgt gctggatgtg ggcggcaact gccgccgctg cgatcatgcg ccgaacccgt   6720
gcatgaatg cccgcgcgcat ttccgcagc tgcatccgga tacctttagc catctgagcc   6780
gcctggaagg cctggtgctg aaagatagca gcctgagcctg gtgaacgcg agctggttc    6840
gcggcctggg caacctgcgc gtgctggatc tgagcgaaaa cttttctgtat aaatgcatta   6900
ccaaaaccaa agcgtttcag ggcctgaccc agctgcgcaa actgaacctg agctttaact   6960
atcagaaacg cgtgagcttt gcgcatctga gcctggcgcc gagctttggc agcctggtgg   7020
cgctgaaaga actggatatg catggcattt ttttcgcag cctggatgaa accaccctgc   7080
gccctggc gccgcctgtg atgctgcaga ccctgcgcct cagatgaac tttattaacc    7140
aggcgcagct gggcatttttt cgcgcgtttc cgggcctgcg ctatgtggat ctgagcgata   7200
accgcattag cggcgcgagc gaactgaccg cgaccatggg cgaagcggat ggcgcgaaa    7260
aagtgtggct gcagccgggc gatctggcgc cggcgcggt ggatacccg agcagcgaag    7320
attttcgccc gaactgcagc accctgaact ttaccctgga tctgagccgc aacaacctgg   7380
tgaccgtgca gccggaaatg tttgcgcagc tgagccatct gcagtgcctg cgcctgagcc   7440
```

-continued

```
ataactgcat tagccaggcg gtgaacggca gccagtttct gccgctgacc ggcctgcagg    7500
tgctggatct gagccataac aaactggatc tgtatcatga acatagcttt accgaactgc    7560
cgcgcctgga agcgctggat ctgagctata acagccagcc gtttggcatg cagggcgtgg    7620
gccataactt tagctttgtg gcgcatctgc gcaccctgcg ccatctgagc ctggcgcata    7680
acaacattca tagccaggtg agccagcagc tgtgcagcac cagcctgccg gcgctggatt    7740
ttagcggcaa cgcgctgggc catatgtggg cggaaggcga tctgtatctg catttttttc    7800
agggcctgag cggcctgatt tggctggatc tgagccagaa ccgcctgcat accctgctgc    7860
cgcagaccct gcgcaacctg ccgaaaagcc tgcaggtgct gcgcctgcgc gataactatc    7920
tggcgttttt taaatggtgg agcctgcatt ttctgccgaa actggaagtg ctggatctgg    7980
cgggcaacca gctgaaagcg ctgaccaacg gcagcctgcc ggcgggcacc cgcctgcgcg    8040
gcctggatgt gagctgcaac agcattagct ttgtggcgcc gggcttttt agcaaagcga    8100
aagaactgcg cgaactgaac ctgagcgcga acgcgctgaa aaccgtggat catagctggt    8160
ttggcccgct ggcgagcgcg ctgcagattc tggatgtgag cgcgaacccg ctgcattgcg    8220
cgtgcggcgc ggcgtttatg gatttctgc tggaagtgca ggcggcggtg ccgggcctgc    8280
cgagccgcgt gaaatgcggc agcccgggcc agctgcaggg cctgagcatt tttgcgcagg    8340
atctgcgcct gtgcctggat gaagcgctga gctgggattg ctttgcgctg agcctgctga    8400
cggtggcgct gggcctgggc gtgccgatgc tgcatcatct gtgcggctgg gatctgtggt    8460
attgctttca tctgtgcctg gcgtgagctgc cgtggccgcg ccgccagagc ggccgcagct    8520
aagatgcgct gccgtatgat gcgtttgtgg tgtttgataa acccagagc gcggtcgcgg    8580
attgggtgta taacgaactg cgcggccagc tggaagaatg ccgcggccgc tgggcgctgc    8640
gcctgtgcct ggaagaacgc gattggctgc cgggcaaaac cctgtttgaa aacctgtggg    8700
cgagcgtgta tggcagccgc aaaaccctgt ttgtgctggc gcataccgat cgcgtgagcg    8760
gcctgctgcg cgcgagcttt ctgctggcgc agcagcgcct gctggaagat cgcaaagatg    8820
tggtggtgct ggtgattctg agcccggatg ccgccgcag ccgctatgtg cgcctgcgcc    8880
agcgcctgtg ccgccagagc gtgctgctgt ggccgcatca gccgagcggc cagcgcagct    8940
tttgggcgca gctgggcatg gcgctgaccc gcgataaacc tcattttttat aaccgcaact    9000
tttgccaggg cccgaccgcg gaagggcgga tcaggcggat cacccaaatc ttgtgacaaa    9060
actcacacat gcccaccgtg cccagcacct gaactcctgg ggggaccgtc agtcttcctc    9120
ttccccccaa aacccaagga caccctcatg atctcccgga cccctgaggt cacatgcgtg    9180
gtggtgggacg tgagccacga agaccctgag gtcaagttca actggtacgt ggacggcgtg    9240
gaggtgcata atgccaagac aaagccgcgg gaggagcagt acaacagcac gtaccgtgtg    9300
gtcagcgtcc tcaccgtcct gcaccaggac tggctgaatg gcaaggagta caagtgcaag    9360
gtctccaaca aagccctccc agcccccatc gagaaaacca tctccaaagc caagggcag    9420
ccccgagaac cacaggtgta caccctgccc ccatccgggg aggagatgac caagaaccag    9480
gtcagcctga cctgcctggt caaaggcttc tatcccagcg acatcgccgt ggagtggag    9540
agcaatgggc agccggagaa caactacaag accacgcctc ccgtgctgga ctccgacggc    9600
tccttcttcc tctacagcaa gctcaccgtg gacaagagca ggtggcagca ggggaacgtc    9660
ttctcatgct ccgtgatgca tgaggctctg cacaaccact acacgcagaa gagcctctcc    9720
ctgtctccgg gtaaatag                                                  9738
```

SEQ ID NO: 10    moltype = DNA length = 7364
FEATURE      Location/Qualifiers
source       1..7364
          mol_type = other DNA
          organism = synthetic construct
SEQUENCE: 10

```
ttctagaata atcaacctct ggattacaaa atttgtgaaa gattgactgg tattcttaac      60
tatgttgctc cttttacgct atgtggatac gctgctttaa tgcctttgta tcatgctatt     120
gcttcccgta tggctttcat tttctcctcc ttgtataaat cctggttgct gtctctttat     180
gaggagttgg gcccgttgt caggcaacgt ggcgtggtgt gcactgtgtt tgctgacgca     240
accccacgg gttgggcat tgccaccacc tgtcagctcc tttccgggac tttcgctttc     300
ccctcccta ttgccacggc ggaactcatc gccgcctgcc ttgcccgctg ctggacaggg     360
gctcggctgt tgggcactga caattccgtg gtgttgtcgg ggaaatcatc gtcctttcct     420
tggctgctcg cctgtgttgc cacctggatt ctgcgcggga cgtccttctg ctacgtccct     480
tcggccctca atccagcgga ccttccttcc cgcggcctgc tgccggctct gcggcctctt     540
ccgcgtcttc gccttcgccc tcagacgagt cggatctccc tttgggccgc ctccccgcct     600
aagcttatcg ataccgtcga gatctaactt gtttatttgca gcttataatg gttacaaata     660
aagcaatagc atcacaaatt tcacaaataa agcatttttt tcactgcatt ctagttgtgg     720
tttgtccaaa ctcatcaatg tatcttatca tgtctggatc tcgacctcga ctagagcatg     780
gctacgtaga taagtagcat ggcgggttaa tcattaacta caaggaaccc ctagtgatgg     840
agttggccac tccctctctg cgcgctcgct cgctcactga ggccgggcga ccaaaggtcg     900
cccgacgccc gggctttgcc cggcggcct cagtgagcga gcgagcgcg cagctggcgt     960
aatagcgaag aggcccgcac cgatcgccct tcccaacagt tgcgcagcct gaatggcgaa    1020
tggaattcca gacgattgag cgtcaaaatg taggtatttc catgagcgtt tcctgttcga    1080
caatggctgg cggtaatatt gttctggata ttaccagcaa ggccgatagt ttgagttctt    1140
ctactcaggc aagtgatgtt attactaatc aaagaagtat tgcgacaacg gttaatttgc    1200
gtgatggaca gactctttta ctcggtggcc tcactgatta taaaaacact tctcaggatt    1260
ctggcgtacc gttcctgtct aaaatccctt aatcggcctc cctgttagc tcccgctctg    1320
attctaacga ggaaagcacg ttatacgtga tcgtcaaagc aaccatagta cgcgccctgt    1380
agcggcgcat taagcgcggc gggtgtggtg gttacgcgca gcgtgaccgc tacacttgcc    1440
agcgccctag cgcccgctcc tttcgctttc ttcccttcct ttctcgccac gttcgccggc    1500
tttccccgtc aagctctaaa tcggggggctc cctttagggt tccgatttag tgctttacgg    1560
cacctcgacc ccaaaaaact tgattagggt gatggttcac gtagtgggcc atcgccctga    1620
tagacggttt ttcgcccttt gacgttggag tccacgttct ttaatagtgg actcttgttc    1680
caaactggaa caacactcaa ccctatctcg gtctattctt ttgatttata agggattttg    1740
ccgatttcgg cctattggtt aaaaaatgag ctgatttaac aaaaatttaa cgcgaatttt    1800
aacaaaatat taacgtttac aatttaaata tttgcttata caatcttcct gttttgggg    1860
cttttctgat tatcaaccgg ggtacatatg attgacatgc tagttttacg attaccgttc    1920
atcgattctc ttgtttgctc cagactctca ggcaatgacc tgatagcctt tgtagagacc    1980
```

```
tctcaaaaat agctaccctc tccggcatga atttatcagc tagaacggtt gaatatcata    2040
ttgatggtga tttgactgtc tccggccttt ctcacccgtt tgaatcttta cctacacatt    2100
actcaggcat tgcatttaaa atatatgagg gttctaaaaa tttttatcct tgcgttgaaa    2160
taaaggcttc tcccgcaaaa gtattacagg gtcataatgt ttttggtaca accgatttag    2220
ctttatgctc tgaggcttta ttgcttaatt ttgctaattc tttgccttgc ctgtatgatt    2280
tattggatgt tggaattcct gatgcggtat tttctcctta cgcatctgtg cggtatttca    2340
caccgcatat ggtgcactct cagtacaatc tgctctgatg ccgcatagtt aagccagccc    2400
cgacacccgc caacccgc tgacgcgccc tgacgggctt gtctgctccc ggcatccgct    2460
tacagacaag ctgtgaccgt ctccgggagc tgcatgtgtc agaggttttc accgtcatca    2520
ccgaaacgcg cgagacgaaa gggcctcgtg atacgcctat ttttataggt taatgtcatg    2580
ataataatgg tttcttagac gtcaggtggc acttttcggg gaaatgtgcg cggaaccccct    2640
atttgtttat ttttctaaat acattcaaat atgtatccgc tcatgagaca taaccctga    2700
taaatgcttc aataatattg aaaaaggaag agtatgagta ttcaacattt ccgtgtcgcc    2760
cttattcct tttttgcggc attttgcctt cctgtttttg ctcacccaga aacgctggtg    2820
aaagtaaaag atgctgaaga tcagttgggt gcacgagtgg gttacatcga actggatctc    2880
aacagcggta agatccttga gagttttcgc cccgaagaac gttttccaat gatgagcact    2940
tttaaagttc tgctatgtgg cgcggtatta tcccgtattg acgccgggca agagcaactc    3000
ggtcgccgca tacactattc tcagaatgac ttggttgagt actcaccagt cacagaaaag    3060
catcttacgg atggcatgac agtaagagaa ttatgcagtg ctgccataac catgagtgat    3120
aacactgcgg ccaacttact tctgacaacg atcggaggac cgaaggagct aaccgctttt    3180
ttgcacaaca tgggggatca tgtaactcgc cttgatcgtt gggaaccgga gctgaatgaa    3240
gccataccaa acgacgagcg tgacaccacg atgcctgtag caatggcaac aacgttgcgc    3300
aaactattaa ctggcgaact acttactcta gcttcccggc aacaattaat agactggatg    3360
gaggcggata aagttgcagg accacttctg cgctcggccc ttccggctgg ctggtttatt    3420
gctgataaat ctggagccgg tgagcgtggg tctcgcggta tcattgcagc actggggcca    3480
gatggtaagc cctcccgtat cgtagttatc tacacgacgg gagtcaggc aactatggat    3540
gaacgaaata gacagatcgc tgagataggt gcctcactga ttaagcattg gtaactgtca    3600
gaccaagttt actcatatat actttagatt gatttaaaac ttcattttta atttaaaagg    3660
atctaggtga agatcctttt tgataatctc atgaccaaaa tcccttaacg tgagttttcg    3720
ttccactgag cgtcagaccc cgtagaaaag atcaaaggat cttcttgaga tcctttttt    3780
ctgcgcgtaa tctgctgctt gcaaacaaaa aaaccaccgc taccagcggt ggtttgtttg    3840
ccggatcaag agctaccaac tctttttccg aaggtaactg gcttcagcag agcgcagata    3900
ccaaatactg tccttctagt gtagccgtag ttaggccacc acttcaagaa ctctgtagca    3960
ccgcctacat acctcgctct gctaatcctg ttaccagtgg ctgctgccag tggcgataag    4020
tcgtgtctta ccgggttgga ctcaagacga tagttaccgg ataaggcgca gcggtcgggc    4080
tgaacggggg gttcgtgcac acagcccagc ttggagcgaa cgacctacac cgaactgaga    4140
tacctacagc gtgagctatg agaaagcgcc acgcttcccg aagggagaaa ggcggacagg    4200
tatccggtaa gcggcagggt cggaacagga gagcgcacga gggagcttcc agggggaaac    4260
gcctggtatc tttatagtcc tgtcgggttt cgccacctct gacttgagcg tcgatttttg    4320
tgatgctcgt caggggggcg gagcctatgg aaaaacgcca gcaacgcggc ctttttacgg    4380
ttcctggcct tttgctggcc ttttgctcac atgttcttc ctgcgttatc ccctgattct    4440
gtggataacc gtattaccgc ctttgagtga gctgataccg ctcgccgcag ccgaacgacc    4500
gagcgcagcg agtcagtgag cgaggaagcg gaagagcgcc caatacgcaa accgcctctc    4560
cccgcgcgtt ggccgattca ttaatgcagc agctgcgcgc tcgctcgctc actgaggccg    4620
cccgggcaaa gcccgggcgt cgggcgacct tggtcgcccc ggcctcagtg agcgagcgag    4680
cgcgcagaga gggagtggcc aactccatca ctaggggttc cttgtagtta atgattaacc    4740
cgcgcatgcta cttatctacg tagccatgct ctaggacatt gattattgac tagtggagtt    4800
ccgcgttaca taacttacgg taaatgcccc gcctggctga ccgcccaacg accccccgccc    4860
attgacgtca ataatgacgt atgttccat agtaacgcca atagggactt tccattgacg    4920
tcaatgggtg gagtatttac ggtaaactgc ccacttggca gtacatcaag tgtatcatat    4980
gccaagtacg cccctattg acgtcaatga cggtaaatgg cccgcctggc attatgccca    5040
gtacatgacc ttatgggact ttcctacttg gcagtacatc tacgtattag tcatcgctat    5100
taccatggtc gaggtgagcc cacgttctg cttcactctc cccatctccc ccccctcccc    5160
accccaatt ttgtatttat ttattttta attatttgt gcagcgatgg gggcgggggg    5220
gggggggc gcgcgccagg cggggcgggg cggggcgagg ggcgggcgg ggcgagcggg    5280
agaggtgcgg cggcagccaa tcagagcggc gcgctccgaa agtttccttt tatggcgagg    5340
cggcggcggc ggcggcccta taaaagcga agcgcgcggc gggcgggagt cgctgcgcgc    5400
tgccttcgcc ccgtgcccg ctccgccgcc gcctcgcgcc gcccgccccg gctctgactg    5460
accgcgttac taaaacaggt aagtccggcc tccgcgccgg gttttggcgc ctcccgcggg    5520
cgcccccctc ctcacggcga gcgctgccac gtcagacgaa gggcgcagcg agcgtcctga    5580
tccttccgcc cggacgctca ggacagcggc ccgctgctca taagactcgg ccttagaacc    5640
ccagtatcag cagaaggaca tttaggacg ggacttgggt gactctaggg cactggtttt    5700
ctttccagag agcggaacag gcgaggaaaa gtagtcccct tctcggcgat tctgcggaggg    5760
atctccgtgg ggcggtgaac gccgatgatg cctctactaa ccatgttcat gttttcttt    5820
ttttttctaca ggtcctgggt gacgaacagg gtaccgccac catgagggc atgaagctgc    5880
tgggggcgct gctgctactg gcggccctac tgcagggggc cgtgtccatg agcatgctgt    5940
tttatccct gattaccgcg tttctgattg gcattcaggc ggaaccgcat agcgaaagca    6000
acgtgccggc gggccatacc attccgcagg cgcattggac caaactgcag catagcctgg    6060
ataccgcgct gcgccgcgcg cgcagcgcgc cggcggccgc gattgcgg gcgcgtggcgg    6120
gccagacccg caacattacc gtggatccgc gcctgtttaa aaaacgccgc ctgcgcagcc    6180
cgcgcgtgct gtttagcacc cagcgccgc gcgaagcggc ggataccag gatctggatt    6240
tgaagtgggg cggcgcggcg ccgtttaacc gcacccatcg cagcaaacgc agcagcagcc    6300
atccgatttt tcatcgcggc gaatttagcg tgtgcgatag cgtgagcgtg tgggtgggcg    6360
ataaaaccgc cgcgaccgat attaaaggca aagaagtgat ggtgctgggc gaagtgaaca    6420
ttaacaacag cgtgttaaa cagtatttt ttgaaaccaa atgccgcgat ccgaacccgg    6480
tggatagcgc ctgccgcggc attgatagca aacattggaa cagctattgc accaccaccc    6540
ataccctgt gaaagcgctg accatggatg gcaaacaggc ggcgtggcgc tttattcgca    6600
ttgataccgc gtgcgtgtgc gtgctgagcc gcaaagcggt gcgccgcgcg gcggatcag    6660
gcggatcacc caaatcttgt gacaaaactc acacatgccc accgtgccca gcacctgaac    6720
```

```
tcctgggggg accgtcagtc ttcctcttcc ccccaaaacc caaggacacc ctcatgatct   6780
cccggacccc tgaggtcaca tgcgtggtgg tggacgtgag ccacgaagac cctgaggtca   6840
agttcaactg gtacgtggac ggcgtggagg tgcataatgc caagacaaag ccgcggggag   6900
agcagtacaa cagcacgtac cgtgtggtca gcgtcctcac cgtcctgcac caggactggc   6960
tgaatggcaa ggagtacaag tgcaaggtct ccaacaaagc cctcccagcc cccatcgaga   7020
aaaccatctc caaagccaaa gggcagcccc gagaaccaca ggtgtacacc ctgcccccat   7080
cccgggagga tgaccaag aaccaggtca gcctgacctg cctggtcaaa ggcttctatc     7140
ccagcgacat cgccgtggag tgggagagca atgggcagcc ggagaacaac tacaagacca   7200
cgcctcccgt gctggactcc gacggctcct tcttcctcta cagcaagctc accgtggaca   7260
agagcaggtg gcagcagggg aacgtcttct catgctccgt gatgcatgag gctctgcaca   7320
accactacac gcagaagagc ctctccctgt ctccgggtaa atag                    7364

SEQ ID NO: 11          moltype = DNA  length = 6972
FEATURE                Location/Qualifiers
source                 1..6972
                       mol_type = other DNA
                       organism = synthetic construct
SEQUENCE: 11
ttctagaata atcaacctct ggattacaaa atttgtgaaa gattgactgg tattcttaac     60
tatgttgctc cttttacgct atgtggatac gctgctttaa tgcctttgta tcatgctatt    120
gcttcccgta tggctttcat tttctcctcc ttgtataaat cctggttgct gtctctttat    180
gaggagttgt ggcccgttgt caggcaacgt ggcgtggtgt gcactgtgtt tgctgacgca    240
accccccactg gttggggcat tgccaccacc tgtcagctcc tttccgggac tttcgctttc    300
ccctccctta ttgccacggc ggaactcatc gccgctgcc ttgcccgctg ctggacaggg     360
gctcggctgt tgggcactga caattccgtg gtgttgtcgg ggaaatcatc gtcctttcct    420
tggctgctcg cctgtgttgc cacctggatt ctgcgcggaa cgtccttctg ctacgtcccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatga   840
agttggccac tccctctctg cgcgctcgct cgctcactga ggccgggcga ccaaaggtcg   900
cccgacgccc gggctttgcc cgggcggcct cagtgagcga gcgagcgcgc cagctggcgt   960
aatagcgaag aggcccgcac cgatcgccct tcccaacagt tgcgcagcct gaatggcgaa   1020
tggaattcca gacgattgag cgtcaaaatg taggtatttc catgagcgtt tttcctgttg   1080
caatggctgg cggtaatatt gttctggata ttaccagcaa ggccgatagt ttgagttctt   1140
ctactcaggc aagtgatgtt attactaatc aaagaagtat tgcgacaacg gttaatttgc   1200
gtgatggaca gactctttta ctcggtggcc tcactgatta taaaaacact tctcaggatt   1260
ctggcgtacc gttcctgtct aaaatccctt taatcggcct cctgtttagc tcccgctctg   1320
attctaacga ggaaagcacg ttatacgtgt cgtcaaagc aaccatagta cgcgccctgt     1380
agcggcgcat taagcgcggc gggtgtggtg gttacgcgca gcgtgaccgc tacacttgcc   1440
agcgccctag cgcccgctcc tttcgctttc ttcccttcct ttctcgccac gttcgccggc   1500
tttccccgtc aagctctaaa tcgggggctc cctttagggt tccgatttag tgctttacgg   1560
cacctcgacc ccaaaaaact tgattagggt gatggttcac gtagtgggcc atcgccctga   1620
tagacggttt ttcgcccttt gacgttggag tccacgttct ttaatagtgg actcttgttc   1680
caaactggaa caacactcaa ccctatctcg gtctattctt ttgatttata gggattttg    1740
ccgatttcgg cctattggtt aaaaaatgag ctgatttaac aaaaatttaa cgcgaatttt   1800
aacaaaatat taacgtttac aatttaaata tttgcttata caatcttcct gttttttggg   1860
cttttctgat tatcaaccgg ggtacatatg attgacatgc tagttttacg attaccgttc   1920
atcgattctc ttgtttgctc cagactctca ggcaatgacc tgatagcctt tgtagagacc   1980
tctcaaaaat agctaccctc tccggcatga atttatcagc tagaacggtt gaatatcata   2040
ttgatggtga tttgactgtc tccggccttt ctcacccgtt tgaatcttta cctacacatt   2100
actcaggcat tgcatttaaa atatatgagg gttctaaaaa tttttatcct tgcgttgaaa   2160
taaaggcttc tcccgcaaaa gtattacagg gtcataattt tttggtaca accgatttag    2220
ctttatgctc tgaggcttta ttgcttaatt ttgctaattc tttgccttgc ctgtatgatt   2280
tattggatgt tggaattcct gatgcggtat tttctcctta cgcatctgtg cggtatttca   2340
caccgcatat ggtgcactct cagtacaatc tgctctgatg ccgcatagtt aagccagccc   2400
cgacacccgc caacacccgc tgacgcgccc tgacgggctt gtctgctccc ggcatccgct   2460
tacagacaag ctgtgaccgt ctccgggagc tgcatgtgtc agaggttttc accgtcatca   2520
ccgaaacgcg cgagacgaaa gggcctcgtg atacgcctat ttttataggt taatgtcatg   2580
ataataatgg tttcttagac gtcaggtggc acttttcggg gaaatgtgcg cggaacccct   2640
atttgtttat ttttctaaat acattcaaat atgtatccgc tcatgagaca ataaccctga   2700
taaatgcttc aataatattg aaaaaggaag agtatgagta ttcaacattt ccgtgtcgcc   2760
cttattccct ttttttgcggc attttgcctt cctgtttttg ctcacccaga aacgctggtg   2820
aaagtaaaag atgctgaaga tcagttgggt gcacgagtgg gttacatcga actggatctc   2880
aacagcggta agatccttga gagttttcgc cccgaagaac gttttccaat gatgagcact   2940
tttaaagttc tgctatgtgg cgcggtatta tcccgtattg acgccgggca agagcaactc   3000
ggtcgccgca tacactattc tcagaatgac ttggttgagt actcaccagt cacagaaaag   3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc   3300
aaactattac tggcgaact acttactcta gcttcccggc aacaattaat agactggatg   3360
gaggcggata aagttgcagg accacttctg cgctcggccc ttccggctgg ctggtttatt   3420
gctgataaat ctggagccgg tgagcgtggg tctcgcggta tcattgcagc actggggcca   3480
gatggtaagc cctcccgtat cgtagttatc tacacgacgg ggagtcaggc aactatggat   3540
gaacgaaata gacagatcgc tgagataggt gcctcactga ttaagcattg gtaactgtca   3600
gaccaagttt actcatatat actttagatt gatttaaaac ttcattttta atttaaaagg   3660
```

```
atctaggtga agatcctttt tgataatctc atgaccaaaa tcccttaacg tgagttttcg   3720
ttccactgag cgtcagaccc cgtagaaaag atcaaaggat cttcttgaga tcctttttt    3780
ctgcgcgtaa tctgctgctt gcaaacaaaa aaaccaccgc taccagcggt ggtttgtttg   3840
ccggatcaag agctaccaac tcttttccg aaggtaactg gcttcagcag agcgcagata    3900
ccaaatactg tccttctagt gtagccgtag ttaggccacc acttcaagaa ctctgtagca   3960
ccgcctacat acctcgctct gctaatcctg ttaccagtgg ctgctgccag tggcgataag   4020
tcgtgtctta ccgggttgga ctcaagacga tagttaccgg ataaggcgca gcggtcgggc   4080
tgaacggggg gttcgtgcac acagcccagc ttggagcgaa cgacctacac cgaactgaga   4140
tacctacagc gtgagctatg agaaagcgcc acgcttcccg aagggagaaa ggcggacagg   4200
tatccggtaa gcggcagggt cggaacagga gagcgcacga gggagcttcc aggggggaaac  4260
gcctggtatc tttatagtcc tgtcgggttt cgccacctct gacttgagcg tcgatttttg   4320
tgatgctcgt caggggggcg gagcctatgg aaaaacgcca gcaacgcggc cttttacgg    4380
ttcctggcct tttgctggcc ttttgctcac atgttctttc ctgcgttatc ccctgattct   4440
gtggataacc gtattaccgc ctttgagtga gctgataccg ctcgccgcag ccgaacgacc   4500
gagcgcagcg agtcagtgag cgaggaagcg gaagagcgcc caatacgcaa accgcctctc   4560
cccgcgcgtt ggccgattca ttaatgcagc agctgcgcgc tcgctcgctc actgaggccg   4620
cccgggcaaa gcccggcgt cgggcgacct ttggtcgccc ggcctcagtg agcgagcgag    4680
cgcgcagaga gggagtggcc aactccatca ctaggggttc cttgtagtta atgattaacc   4740
cgccatgcta cttatctacg tagccatgct ctaggacatt gattattgac tagtggagtt   4800
ccgcgttaca taacttacgg taaatggccc gcctggctga ccgcccaacg accccgccc    4860
attgacgtca ataatgacgt atgttcccat agtaacgcca atagggactt tccattacg    4920
tcaatgggtg gagtatttac ggtaaactgc ccacttggca gtacatcaag tgtatcatat   4980
gccaagtacg ccccctattg acgtcaatga cggtaaatgg cccgcctggc attatgccca   5040
gtacatgacc ttatgggact ttcctacttg gcagtacatc tacgtattag tcatcgctat   5100
taccatggtc gaggtgagcc ccacgttctg cttcactctc cccatctccc cccctcccc    5160
accccaatt ttgtatttat ttattttta attattttgt gcagcgatgg gggcgggggg     5220
ggggggggc gcgcgccagg cggggcgggg cggggcgagg ggcggggcgg ggcgaggcgg    5280
agaggtcgcg cggcagccaa tcagagcggc gcgctccgaa agtttccttt tatggcgagg   5340
cggcggcggc ggcggcccta taaaagcga agcgcgcggc gggcgggagt cgctgcgcgc    5400
tgccttcgcc ccgtgcccg ctccgccgcc gcctcgccgc ccccgcccg gctctgactg     5460
accgcgttac taaacaggt aagtccggcc tccgcgccgg gttttggcgc ctcccgcggg    5520
cgcccccctc ctcacggcga gcgctgccac gtcagacgaa gggcgcagcg agcgtcctga   5580
tccttccgcc cggacgctca ggacagcggc ccgctgctca taagactcgg ccttagaacc   5640
ccagtatcag cagaaggaca ttttaggacg ggacttgggt gactctaggg cactggttt    5700
ctttccagag agcggaacag gcgaggaaaa gtagtccctt ctcggcgatt ctgcggaggg   5760
atctccgtgg ggcggtgaac gccgatgatg cctctactaa ccatgttcat gttttctttt   5820
tttttctaca ggtcctgggt gacgaacagg gtaccgccac catgagggc atgaagctgc    5880
tgggggcgct gctggcactg gcggcctac tgcaggggc cgtgtccatg gcgctgtgga    5940
tgcgctgct gccgctgctg gcgctgctgg cgctgtgggg cccggatccg gcggcggcgt   6000
ttgtgaacca gcatcgtgc ggcagccatc tggtggaagc gctgtatctg gtgtgcggcg   6060
aacgcggctt ttttatacc ccgaaaaccc gccgcgaagc ggaagatctg caggtgggcc    6120
aggtggaact gggcggcggc ccgggcgcgg gcagcctgca gccgctggcg ctggaaggca   6180
gcctgcagaa acgcggcatt gtggaacagt gctgcaccag catttgcagc ctgtatcagc   6240
tggaaaacta ttgcaacggg cggatcaggc ggatcaccca aatcttgtga caaaactcac   6300
acatgcccac cgtgcccagc acctgaactc ctggggggac cgtcagtctt cctcttcccc   6360
ccaaaaccca aggacaccct catgatctcc cggacccctg aggtcacatg cgtggtggtg   6420
gacgtgagcc acgaagaccc tgaggtcaag ttcaactggt acgtggacgg cgtggaggtg   6480
cataatgcca agacaaagcc gcgggaggag cagtacaaca gcacgtaccg tgtggtcagc   6540
gtcctcaccg tcctgcacca ggactggctg aatggcaagg agtacaagtg caaggtctcc   6600
aacaaagccc tcccagcccc catcgagaaa accatctcca aagccaaagg gcagcccga    6660
gaaccacagg tgtacaccct gcccccatcc cgggaggaga tgaccaagaa ccaggtcagc   6720
ctgacctgcc tggtcaaagg cttctatccc agcgacatcg ccgtggagtg ggagagcaat   6780
gggcagccgg agaacaacta caagaccacg cctcccgtgc tggactccga cggctccttc   6840
ttcctctaca gcaagctcac cgtggacaag agcaggtggc agcagggaa cgtcttctca    6900
tgctccgtga tgcatgaggc tctgcacaac cactacacg agaagagcct ctccctgtct    6960
ccgggtaaat ag                                                       6972
```

US 12,416,020 B2

PLASMID ENCODING A TLR3 AND Fc FUSION PROTEIN

This application contains a Sequence Listing electronically submitted via Patent Center to the United States Patent and Trademark Office as an XML Document file entitled "A8149440US-Sequence Listing.xml" created on 2024 Feb. 8 and having a size of 68,245 bytes. The information contained in the Sequence Listing is incorporated by reference herein.

TECHNICAL FIELD

The present disclosure generally relates to compositions for regulating the production of fusion proteins. In particular, the present disclosure relates to compositions for regulating gene expression and, consequently, the production of fusion proteins.

BACKGROUND

Bioactive molecules, including toll-like receptors, enzymes, and hormones, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and the regulation of bioactive molecules are lost in order to prevent or treat the resulting disease.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a fusion protein with an Fc fragment, such as a toll-like receptor 3-Fc (TLR3-Fc). In some embodiments of the present disclosure, the target biomolecule is toll-like receptor 9-Fc (TLR9-Fc). In some embodiments of the present disclosure, the target biomolecule is deoxyribonuclease I-Fc (DNAse I-Fc). In some embodiments of the present disclosure, the target biomolecule is neural growth factor-Fc (NGF-Fc). In some embodiments of the present disclosure, the target biomolecule is insulin-Fc.

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for the fusion protein DNAse I-Fc.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding an mRNA sequence that encodes for the fusion protein TLR3-Fc.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding an mRNA sequence that encodes for the fusion protein TLR9-Fc.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding an mRNA sequence that encodes for the fusion protein NGF-Fc.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding an mRNA sequence that encodes for the fusion protein insulin-Fc.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5 or SEQ ID NO. 6 to a target cell for forming the composition/target cell complex, wherein the composition/target cell complex causes the target cell to increase production of one or more sequences of mRNA that increases production of a target biomolecule.

Embodiments of the present disclosure relate to at least one approach for inducing endogenous production of one or more sequences of mRNA that encodes for a target biomolecule, for example TLR3-Fc. A first approach utilizes gene vectors containing nucleotide sequences for increasing the endogenous production of one or more sequences of mRNA, which are complete or partial sequences and/or combinations thereof of TLR3-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example TLR9-Fc. A first approach utilizes gene vectors containing nucleotide sequences for increasing the endogenous production of one or more sequences of mRNA, which are complete or partial sequences and/or combinations thereof of TLR9-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example DNAse I-Fc. A first approach utilizes gene vectors containing nucleotide sequences for increasing the endogenous production of one or more sequences of mRNA, which are complete or partial sequences and/or combinations thereof of DNAse I-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example NGF-Fc. A first approach utilizes gene vectors containing nucleotide sequences for increasing the endogenous production of one or more sequences of mRNA, which are complete or partial sequences and/or combinations thereof of NGF-Fc, which can be administered to a subject to increase the subject's production of one or more sequences of the mRNA.

Embodiments of the present disclosure relate to at least one approach for inducing endogenous production of one or more sequences of mRNA that encodes for a target biomolecule, for example insulin-Fc. A first approach utilizes gene vectors containing nucleotide sequences for increasing the endogenous production of one or more sequences of mRNA, which are complete or partial sequences and/or combinations thereof of insulin-Fc, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein-Fc fusion molecule that is found within a subject. A biomolecule may be endogenous or exogenous to a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a fusion protein with an Fc fragment. An Fc fragment is the distal portion of the heavy chain of an antibody.

In some embodiments of the present disclosure, the target biomolecule is TLR3-Fc.

In some embodiments of the present disclosure, the target biomolecule is TLR9-Fc.

In some embodiments of the present disclosure, the target biomolecule is DNAse I-Fc.

In some embodiments of the present disclosure, the target biomolecule is NGF-Fc.

In some embodiments of the present disclosure, the target biomolecule is insulin-Fc.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as TLR3-Fc, TLR9-Fc, DNAse I-Fc, NGF-Fc or insulin-Fc.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of a RP that when operable inside a target cell will cause the target cell to produce a mRNA sequence that upregulates production of a biomolecule, with examples being TLR3-Fc, TLR9-Fc, DNAse I-Fc, NGF-Fc, or insulin-Fc. The RP is comprised of AAV2 inverted terminal repeats (ITRs), a composite CASI promoter, and a human growth hormone (HGH) signal peptide followed by a mRNA expression cassette encoding for TLR3-Fc, TLR9-Fc, DNAse I-Fc, NGF-Fc, or insulin-Fc, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):

5'

TTCTAGAATAATCAACCTCTGGATTACAAAATTTGTGAAAGATTGACTGGTATTCTT

-continued

```
AACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTGCTGTCT
CTTTATGAGGAGTTGTGGCCCGTTGTCAGGCAACGTGGCGTGGTGTGCACTGTGTTT
GCTGACGCAACCCCCACTGGTTGGGGCATTGCCACCACCTGTCAGCTCCTTTCCGGG
ACTTTCGCTTTCCCCCTCCCTATTGCCACGGCGGAACTCATCGCCGCCTGCCTTGCCC
GCTGCTGGACAGGGGCTCGGCTGTTGGGCACTGACAATTCCGTGGTGTTGTCGGGGA
AATCATCGTCCTTTCCTTGGCTGCTCGCCTGTGTTGCCACCTGGATTCTGCGCGGGAC
GTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCT
CCCTTTGGGCCGCCTCCCCGCCTAAGCTTATCGATACCGTCGAGATCTAACTTGTTTA
TTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
GTCTGGATCTCGACCTCGACTAGAGCATGGCTACGTAGATAAGTAGCATGGCGGGTT
AATCATTAACTACAAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCC
GGGCGGCCTCAGTGAGCGAGCGAGCGCGCCAGCTGGCGTAATAGCGAAGAGGCCC
GCACCGATCGCCCTTCCCAACAGTTGCGCAGCCTGAATGGCGAATGGAATTCCAGA
CGATTGAGCGTCAAAATGTAGGTATTTCCATGAGCGTTTTTCCTGTTGCAATGGCTG
GCGGTAATATTGTTCTGGATATTACCAGCAAGGCCGATAGTTTGAGTTCTTCTACTC
AGGCAAGTGATGTTATTACTAATCAAAGAAGTATTGCGACAACGGTTAATTTGCGTG
ATGGACAGACTCTTTTACTCGGTGGCCTCACTGATTATAAAAACACTTCTCAGGATT
CTGGCGTACCGTTCCTGTCTAAAATCCCTTTAATCGGCCTCCTGTTTAGCTCCCGCTC
TGATTCTAACGAGGAAAGCACGTTATACGTGCTCGTCAAAGCAACCATAGTACGCG
CCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGA
TTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTT
GCTTATACAATCTTCCTGTTTTTGGGGCTTTTCTGATTATCAACCGGGGTACATATGA
TTGACATGCTAGTTTTACGATTACCGTTCATCGATTCTCTTGTTTGCTCCAGACTCTC
AGGCAATGACCTGATAGCCTTTGTAGAGACCTCTCAAAAATAGCTACCCTCTCCGGC
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
```

-continued

```
TGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGCGG
AGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGT
TGGCCGATTCATTAATGCAGCAGCTGCGCGCTCGCTCGCTCACTGAGGCCGCCCGGG
CAAAGCCCGGGCGTCGGGCGACCTTTGGTCGCCCGGCCTCAGTGAGCGAGCGAGCG
```

-continued

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGCGGGGGGGGGGGGGCGCGCGCCAGGCGGGGCGGGGGGG

GCGAGGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACCGCCACC

3'

SEQ ID NO. 2 (mRNA expression cassette No. 2 - DNAse I-Fc):
5'

ATGAGGGGCATGAAGCTGCTGGGGGCGCTGCTGGCACTGGCGGCCCT

ACTGCAGGGGGCCGTGTCCCTGAAGATCGCAGCCTTCAACATCCAGACATTTGGGG

AGACCAAGATGTCCAATGCCACCCTCGTCAGCTACATTGTGCAGATCCTGAGCCGCT

ATGACATCGCCCTGGTCCAGGAGGTCAGAGACAGCCACCTGACTGCCGTGGGGAAG

CTGCTGGACAACCTCAATCAGGATGCACCAGACACCTATCACTACGTGGTCAGTGA

GCCACTGGGACGGAACAGCTATAAGGAGCGCTACCTGTTCGTGTACAGGCCTGACC

AGGTGTCTGCGGTGGACAGCTACTACTACGATGATGGCTGCGAGCCCTGCGGGAAC

GACACCTTCAACCGAGAGCCAGCCATTGTCAGGTTCTTCTCCCGGTTCACAGAGGTC

AGGGAGTTTGCCATTGTTCCCCTGCATGCGGCCCCGGGGGACGCAGTAGCCGAGAT

CGACGCTCTCTATGACGTCTACCTGGATGTCCAAGAGAAATGGGGCTTGGAGGACGT

CATGTTGATGGCGACTTCAATGCGGGCTGCAGCTATGTGAGACCCTCCCAGTGGTC

ATCCATCCGCCTGTGGACAAGCCCCACCTTCCAGTGGCTGATCCCCGACAGCGCTGA

CACCACAGCTACACCCACGCACTGTGCCTATGACAGGATCGTGGTTGCAGGGATGCT

GCTCCGAGGCGCCGTTGTTCCCGACTCGGCTCTTCCCTTTAACTTCCAGGCTGCCTAT

GGCCTGAGTGACCAACTGGCCCAAGCCATCAGTGACCACTATCCAGTGGAGGTGAT

GCTGAAGGGCGGATCAGGCGGATCACCCAAATCTTGTGACAAAACTCACACATGCC

CACCGTGCCCAGCACCTGAACTCCTGGGGGGACCGTCAGTCTTCCTCTTCCCCCCAA

-continued

AACCCAAGGACACCCTCATGATCTCCCGGACCCCTGAGGTCACATGCGTGGTGGTG

GACGTGAGCCACGAAGACCCTGAGGTCAAGTTCAACTGGTACGTGGACGGCGTGGA

GGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAA

GTGCAAGGTCTCCAACAAAGCCCTCCCAGCCCCCATCGAGAAAACCATCTCCAAAG

CCAAAGGGCAGCCCCGAGAACCACAGGTGTACACCCTGCCCCCATCCCGGGAGGAG

ATGACCAAGAACCAGGTCAGCCTGACCTGCCTGGTCAAAGGCTTCTATCCCAGCGA

CATCGCCGTGGAGTGGGAGAGCAATGGGCAGCCGGAGAACAACTACAAGACCACG

CCTCCCGTGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGAGGCTCT

GCACAACCACTACACGCAGAAGAGCCTCTCCCTGTCTCCGGGTAAATAG

3'

SEQ ID NO. 3 (mRNA expression cassette No. 3 - TLR3-Fc):
5'

GCCAGACCCTGCCGTGCATTTATTTTTGGGGCGGCCTGCTGCCGTTTGGCATGCTGTG

CGCGAGCAGCACCACCAAATGCACCGTGAGCCATGAAGTGGCGGATTGCAGCCATC

TGAAACTGACCCAGGTGCCGGATGATCTGCCGACCAACATTACCGTGCTGAACCTG

ACCCATAACCAGCTGCGCCGCCTGCCGGCGGCGAACTTTACCCGCTATAGCCAGCTG

ACCAGCCTGGATGTGGGCTTTAACACCATTAGCAAACTGGAACCGGAACTGTGCCA

GAAACTGCCGATGCTGAAAGTGCTGAACCTGCAGCATAACGAACTGAGCCAGCTGA

GCGATAAAACCTTTGCGTTTTGCACCAACCTGACCGAACTGCATCTGATGAGCAACA

GCATTCAGAAAATTAAAAACAACCCGTTTGTGAAACAGAAAAACCTGATTACCCTG

GATCTGAGCCATAACGGCCTGAGCAGCACCAAACTGGGCACCCAGGTGCAGCTGGA

AAACCTGCAGGAACTGCTGCTGAGCAACAACAAAATTCAGGCGCTGAAAAGCGAAG

AACTGGATATTTTTGCGAACAGCAGCCTGAAAAAACTGGAACTGAGCAGCAACCAG

ATTAAAGAATTTAGCCCGGGCTGCTTTCATGCGATTGGCCGCCTGTTTGGCCTGTTTC

TGAACAACGTGCAGCTGGGCCCGAGCCTGACCGAAAAACTGTGCCTGGAACTGGCG

AACACCAGCATTCGCAACCTGAGCCTGAGCAACAGCCAGCTGAGCACCACCAGCAA

CACCACCTTTCTGGGCCTGAAATGGACCAACCTGACCATGCTGGATCTGAGCTATAA

CAACCTGAACGTGGTGGGCAACGATAGCTTTGCGTGGCTGCCGCAGCTGGAATATTT

TTTTCTGGAATATAACAACATTCAGCATCTGTTTAGCCATAGCCTGCATGGCCTGTTT

AACGTGCGCTATCTGAACCTGAAACGCAGCTTTACCAAACAGAGCATTAGCCTGGC

GAGCCTGCCGAAAATTGATGATTTTAGCTTTCAGTGGCTGAAATGCCTGGAACATCT

GAACATGGAAGATAACGATATTCCGGGCATTAAAAGCAACATGTTTACCGGCCTGA

TTAACCTGAAATATCTGAGCCTGAGCAACAGCTTTACCAGCCTGCGCACCCTGACCA

ACGAAACCTTTGTGAGCCTGGCGCATAGCCCGCTGCATATTCTGAACCTGACCAAAA

ACAAAATTAGCAAAATTGAAAGCGATGCGTTTAGCTGGCTGGGCCATCTGGAAGTG

CTGGATCTGGGCCTGAACGAAATTGGCCAGGAACTGACCGGCCAGGAATGGCGCGG

CCTGGAAAACATTTTTGAAATTTATCTGAGCTATAACAAATATCTGCAGCTGACCCG

CAACAGCTTTGCGCTGGTGCCGAGCCTGCAGCGCCTGATGCTGCGCCGCGTGGCGCT

GAAAAACGTGGATAGCAGCCCGAGCCCGTTTCAGCCGCTGCGCAACCTGACCATTC

-continued

```
TGGATCTGAGCAACAACAACATTGCGAACATTAACGATGATATGCTGGAAGGCCTG

GAAAAACTGGAAATTCTGGATCTGCAGCATAACAACCTGGCGCGCCTGTGGAAACA

TGCGAACCCGGGCGGCCCGATTTATTTTCTGAAAGGCCTGAGCCATCTGCATATTCT

GAACCTGGAAAGCAACGGCTTTGATGAAATTCCGGTGGAAGTGTTTAAAGATCTGTT

TGAACTGAAAATTATTGATCTGGGCCTGAACAACCTGAACACCCTGCCGGCGAGCGT

GTTTAACAACCAGGTGAGCCTGAAAAGCCTGAACCTGCAGAAAAACCTGATTACCA

GCGTGGAAAAAAAAGTGTTTGGCCCGGCGTTTCGCAACCTGACCGAACTGGATATG

CGCTTTAACCCGTTTGATTGCACCTGCGAAAGCATTGCGTGGTTTGTGAACTGGATT

AACGAAACCCATACCAACATTCCGGAACTGAGCAGCCATTATCTGTGCAACACCCC

GCCGCATTATCATGGCTTTCCGGTGCGCCTGTTTGATACCAGCAGCTGCAAAGATAG

CGCGCCGTTTGAACTGTTTTTTATGATTAACACCAGCATTCTGCTGATTTTTATTTTTA

TTGTGCTGCTGATTCATTTTGAAGGCTGGCGCATTAGCTTTTATTGGAACGTGAGCGT

GCATCGCGTGCTGGGCTTTAAAGAAATTGATCGCCAGACCGAACAGTTTGAATATGC

GGCGTATATTATTCATGCGTATAAAGATAAAGATTGGGTGTGGGAACATTTTAGCAG

CATGGAAAAAGAAGATCAGAGCCTGAAATTTTGCCTGGAAGAACGCGATTTTGAAG

CGGGCGTGTTTGAACTGGAAGCGATTGTGAACAGCATTAAACGCAGCCGCAAAATT

ATTTTTGTGATTACCCATCATCTGCTGAAAGATCCGCTGTGCAAACGCTTTAAAGTG

CATCATGCGGTGCAGCAGGCGATTGAACAGAACCTGGATAGCATTATTCTGGTGTTT

CTGGAAGAAATTCCGGATTATAAACTGAACCATGCGCTGTGCCTGCGCCGCGGCATG

TTTAAAAGCCATTGCATTCTGAACTGGCCGGTGCAGAAAGAACGCATTGGCGCGTTT

CGCCATAAACTGCAGGTGGCGCTGGGCAGCAAAAACAGCGTGCATGGGCGGATCAG

GCGGATCACCCAAATCTTGTGACAAAACTCACACATGCCCACCGTGCCCAGCACCTG

AACTCCTGGGGGGACCGTCAGTCTTCCTCTTCCCCCCAAAACCCAAGGACACCCTCA

TGATCTCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCG

TCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGA

ACCACAGGTGTACACCCTGCCCCCATCCCGGGAGGAGATGACCAAGAACCAGGTCA

GCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGA

CGGCTCCTTCTTCCTCTACAGCAAGCTCACCGTGGACAAGAGCAGGTGGCAGCAGG

GGAACGTCTTCTCATGCTCCGTGATGCATGAGGCTCTGCACAACCACTACACGCAGA

AGAGCCTCTCCCTGTCTCCGGGTAAATAG

3'

SEQ ID NO. 4 (miRNA expression cassette No. 4 - TLR9-Fc):
5'

ATGAGGGGCATGAAGCTGCTGGGGGCGCTGCTGGCACTGGCGGCCCTACTGCAGGG

GGCCGTGTCCATGGGCTTTTGCCGCAGCGCGCTGCATCCGCTGAGCCTGCTGGTGCA

GGCGATTATGCTGGCGATGACCCTGGCGCTGGGCACCCTGCCGGCGTTTCTGCCGTG

CGAACTGCAGCCGCATGGCCTGGTGAACTGCAACTGGCTGTTTCTGAAAAGCGTGCC
```

-continued

```
GCATTTTAGCATGGCGGCGCCGCGCGGCAACGTGACCAGCCTGAGCCTGAGCAGCA
ACCGCATTCATCATCTGCATGATAGCGATTTTGCGCATCTGCCGAGCCTGCGCCATC
TGAACCTGAAATGGAACTGCCCGCCGGTGGGCCTGAGCCCGATGCATTTTCCGTGCC
ATATGACCATTGAACCGAGCACCTTTCTGGCGGTGCCGACCCTGGAAGAACTGAAC
CTGAGCTATAACAACATTATGACCGTGCCGGCGCTGCCGAAAAGCCTGATTAGCCTG
AGCCTGAGCCATACCAACATTCTGATGCTGGATAGCGCGAGCCTGGCGGGCCTGCA
TGCGCTGCGCTTTCTGTTTATGGATGGCAACTGCTATTATAAAAACCCGTGCCGCCA
GGCGCTGGAAGTGGCGCCGGGCGCGCTGCTGGGCCTGGGCAACCTGACCCATCTGA
GCCTGAAATATAACAACCTGACCGTGGTGCCGCGCAACCTGCCGAGCAGCCTGGAA
TATCTGCTGCTGAGCTATAACCGCATTGTGAAACTGGCGCCGGAAGATCTGGCGAAC
CTGACCGCGCTGCGCGTGCTGGATGTGGGCGGCAACTGCCGCCGCTGCGATCATGC
GCCGAACCCGTGCATGGAATGCCCGCGCCATTTTCCGCAGCTGCATCCGGATACCTT
TAGCCATCTGAGCCGCCTGGAAGGCCTGGTGCTGAAAGATAGCAGCCTGAGCTGGC
TGAACGCGAGCTGGTTTCGCGGCCTGGGCAACCTGCGCGTGCTGGATCTGAGCGAA
AACTTTCTGTATAAATGCATTACCAAAACCAAAGCGTTTCAGGGCCTGACCCAGCTG
CGCAAACTGAACCTGAGCTTTAACTATCAGAAACGCGTGAGCTTTGCGCATCTGAGC
CTGGCGCCGAGCTTTGGCAGCCTGGTGGCGCTGAAAGAACTGGATATGCATGGCATT
TTTTTTCGCAGCCTGGATGAAACCACCCTGCGCCCGCTGGCGCGCCTGCCGATGCTG
CAGACCCTGCGCCTGCAGATGAACTTTATTAACCAGGCGCAGCTGGGCATTTTTCGC
GCGTTTCCGGGCCTGCGCTATGTGGATCTGAGCGATAACCGCATTAGCGGCGCGAGC
GAACTGACCGCGACCATGGGCGAAGCGGATGGCGGCGAAAAAGTGTGGCTGCAGC
CGGGCGATCTGGCGCCGGCGCCGGTGGATACCCCGAGCAGCGAAGATTTTCGCCCG
AACTGCAGCACCCTGAACTTTACCCTGGATCTGAGCCGCAACAACCTGGTGACCGTG
CAGCCGGAAATGTTTGCGCAGCTGAGCCATCTGCAGTGCCTGCGCCTGAGCCATAAC
TGCATTAGCCAGGCGGTGAACGGCAGCCAGTTTCTGCCGCTGACCGGCCTGCAGGT
GCTGGATCTGAGCCATAACAAACTGGATCTGTATCATGAACATAGCTTTACCGAACT
GCCGCGCCTGGAAGCGCTGGATCTGAGCTATAACAGCCAGCCGTTTGGCATGCAGG
GCGTGGGCCATAACTTTAGCTTTGTGGCGCATCTGCGCACCCTGCGCCATCTGAGCC
TGGCGCATAACAACATTCATAGCCAGGTGAGCCAGCAGCTGTGCAGCACCAGCCTG
CGCGCGCTGGATTTTAGCGGCAACGCGCTGGGCCATATGTGGGCGGAAGGCGATCT
GTATCTGCATTTTTTTCAGGGCCTGAGCGGCCTGATTTGGCTGGATCTGAGCCAGAA
CCGCCTGCATACCCTGCTGCCGCAGACCCTGCGCAACCTGCCGAAAAGCCTGCAGGT
GCTGCGCCTGCGCGATAACTATCTGGCGTTTTTTAAATGGTGGAGCCTGCATTTTCTG
CCGAAACTGGAAGTGCTGGATCTGGCGGGCAACCAGCTGAAAGCGCTGACCAACGG
CAGCCTGCCGGCGGGCACCCGCCTGCCGCCGCTGGATGTGAGCTGCAACAGCATTA
GCTTTGTGGCGCCGGGCTTTTTTAGCAAAGCGAAAGAACTGCGCGAACTGAACCTGA
GCGCGAACGCGCTGAAAACCGTGGATCATAGCTGGTTTGGCCCGCTGGCGAGCGCG
CTGCAGATTCTGGATGTGAGCGCGAACCCGCTGCATTGCGCGTGCGGCGCGGCGTTT
ATGGATTTTCTGCTGGAAGTGCAGGCGGCGGTGCCGGGCCTGCCGAGCCGCGTGAA
ATGCGGCAGCCCGGGCCAGCTGCAGGGCCTGAGCATTTTTGCGCAGGATCTGCGCCT
```

-continued
```
GTGCCTGGATGAAGCGCTGAGCTGGGATTGCTTTGCGCTGAGCCTGCTGGCGGTGGC

GCTGGGCCTGGGCGTGCCGATGCTGCATCATCTGTGCGGCTGGGATCTGTGGTATTG

CTTTCATCTGTGCCTGGCGTGGCTGCCGTGGCGCGGCCGCCAGAGCGGCCGCGATGA

AGATGCGCTGCCGTATGATGCGTTTGTGGTGTTTGATAAAACCCAGAGCGCGGTGGC

GGATTGGGTGTATAACGAACTGCGCGGCCAGCTGGAAGAATGCCGCGGCCGCTGGG

CGCTGCGCCTGTGCCTGGAAGAACGCGATTGGCTGCCGGGCAAAACCCTGTTTGAA

AACCTGTGGGCGAGCGTGTATGGCAGCCGCAAAACCCTGTTTGTGCTGGCGCATACC

GATCGCGTGAGCGGCCTGCTGCGCGCGAGCTTTCTGCTGGCGCAGCAGCGCCTGCTG

GAAGATCGCAAAGATGTGGTGGTGCTGGTGATTCTGAGCCCGGATGGCCGCCGCAG

CCGCTATGTGCGCCTGCGCCAGCGCCTGTGCCGCCAGAGCGTGCTGCTGTGGCCGCA

TCAGCCGAGCGGCCAGCGCAGCTTTTGGGCGCAGCTGGGCATGGCGCTGACCCGCG

ATAACCATCATTTTTATAACCGCAACTTTTGCCAGGGCCCGACCGCGGAAGGGCGGA

TCAGGCGGATCACCCAAATCTTGTGACAAAACTCACACATGCCCACCGTGCCCAGC

ACCTGAACTCCTGGGGGGACCGTCAGTCTTCCTCTTCCCCCCAAAACCCAAGGACAC

CCTCATGATCTCCCGGACCCCTGAGGTCACATGCGTGGTGGTGGACGTGAGCCACGA

AGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTC

ACCGTCCTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGCAGCCCC

GAGAACCACAGGTGTACACCCTGCCCCCATCCCGGGAGGAGATGACCAAGAACCAG

GTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTC

CGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGC

AGAAGAGCCTCTCCCTGTCTCCGGGTAAATAG
```
3'

SEQ ID NO. 5 (mRNA expression cassette No. 5 - NGF-Fc):
5'
```
ATGAGGGGCATGAAGCTGCTGGGGGCGCTGCTGGCACTGGCGGCCCTACTGCAGGG

GGCCGTGTCCATGAGCATGCTGTTTTATACCCTGATTACCGCGTTTCTGATTGGCATT

CAGGCGGAACCGCATAGCGAAAGCAACGTGCCGGCGGGCCATACCATTCCGCAGGC

GCATTGGACCAAACTGCAGCATAGCCTGGATACCGCGCTGCGCCGCGCGCGCAGCG

CGCCGGCGGCGGCGATTGCGGCGCGCGTGGCGGGCCAGACCCGCAACATTACCGTG

GATCCGCGCCTGTTTAAAAAACGCCGCCTGCGCAGCCCGCGCGTGCTGTTTAGCACC

CAGCCGCCGCGCGAAGCGGCGGATACCCAGGATCTGGATTTTGAAGTGGGCGGCGC

GGCGCCGTTTAACCGCACCCATCGCAGCAAACGCAGCAGCAGCCATCCGATTTTTCA

TCGCGGCGAATTTAGCGTGTGCGATAGCGTGAGCGTGTGGGTGGGCGATAAAACCA

CCGCGACCGATATTAAAGGCAAAGAAGTGATGGTGCTGGGCGAAGTGAACATTAAC

AACAGCGTGTTTAAACAGTATTTTTTTGAAACCAAATGCCGCGATCCGAACCCGGTG

GATAGCGGCTGCCGCGGCATTGATAGCAAACATTGGAACAGCTATTGCACCACCAC

CCATACCTTTGTGAAAGCGCTGACCATGGATGGCAAACAGGCGGCGTGGCGCTTTAT
```

```
TCGCATTGATACCGCGTGCGTGTGCGTGCTGAGCCGCAAAGCGGTGCGCCGCGCGG

GCGGATCAGGCGGATCACCCAAATCTTGTGACAAAACTCACACATGCCCACCGTGC

CCAGCACCTGAACTCCTGGGGGACCGTCAGTCTTCCTCTTCCCCCCAAAACCCAAG

GACACCCTCATGATCTCCCGGACCCCTGAGGTCACATGCGTGGTGGTGGACGTGAGC

CACGAAGACCCTGAGGTCAAGTTCAACTGGTACGTGGACGGCGTGGAGGTGCATAA

TGCCAAGACAAAGCCGCGGGAGGAGCAGTACAACAGCACGTACCGTGTGGTCAGCG

TCCTCACCGTCCTGCACCAGGACTGGCTGAATGGCAAGGAGTACAAGTGCAAGGTC

TCCAACAAAGCCCTCCCAGCCCCCATCGAGAAAACCATCTCCAAAGCCAAAGGGCA

GCCCCGAGAACCACAGGTGTACACCCTGCCCCCATCCCGGGAGGAGATGACCAAGA

ACCAGGTCAGCCTGACCTGCCTGGTCAAAGGCTTCTATCCCAGCGACATCGCCGTGG

AGTGGGAGAGCAATGGGCAGCCGGAGAACAACTACAAGACCACGCCTCCCGTGCTG

GACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTAC

ACGCAGAAGAGCCTCTCCCTGTCTCCGGGTAAATAG
```
3'

SEQ ID NO. 6 (mRNA expression cassette No. 6 - insulin-Fc):
5'
```
ATGAGGGGCATGAAGCTGCTGGGGGCGCTGCTGGCACTGGCGGCCCTACTGCAGGG

GGCCGTGTCCATGGCGCTGTGGATGCGCCTGCTGCCGCTGCTGGCGCTGCTGGCGCT

GTGGGGCCCGGATCCGGCGGCGGCGTTTGTGAACCAGCATCTGTGCGGCAGCCATC

TGGTGGAAGCGCTGTATCTGGTGTGCGGCGAACGCGGCTTTTTTTATACCCCGAAAA

CCCGCCGCGAAGCGGAAGATCTGCAGGTGGGCCAGGTGGAACTGGGCGGCGGCCCG

GGCGCGGGCAGCCTGCAGCCGCTGGCGCTGGAAGGCAGCCTGCAGAAACGCGGCAT

TGTGGAACAGTGCTGCACCAGCATTTGCAGCCTGTATCAGCTGGAAAACTATTGCAA

CGGGCGGATCAGGCGGATCACCCAAATCTTGTGACAAAACTCACACATGCCCACCG

TGCCCAGCACCTGAACTCCTGGGGGACCGTCAGTCTTCCTCTTCCCCCCAAAACCC

AAGGACACCCTCATGATCTCCCGGACCCCTGAGGTCACATGCGTGGTGGTGGACGT

GAGCCACGAAGACCCTGAGGTCAAGTTCAACTGGTACGTGGACGGCGTGGAGGTGC

ATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCAA

GGTCTCCAACAAAGCCCTCCCAGCCCCCATCGAGAAAACCATCTCCAAAGCCAAAG

GGCAGCCCCGAGAACCACAGGTGTACACCCTGCCCCCATCCCGGGAGGAGATGACC

AAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGT

GCTGGACTCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGCACAACCA

CTACACGCAGAAGAGCCTCTCCCTGTCTCCGGGTAAATAG
```
3'

SEQ ID NO: 7 = SEQ ID NO: 1 + SEQ ID NO: 2
5'
```
TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG
```

-continued

```
CTATTGCTTCCCGTATGGCTTTCATTTTCTCCTCCTTGTATAAATCCTGGTTGCTGTCT
CTTTATGAGGAGTTGTGGCCCGTTGTCAGGCAACGTGGCGTGGTGTGCACTGTGTTT
GCTGACGCAACCCCCACTGGTTGGGGCATTGCCACCACCTGTCAGCTCCTTTCCGGG
ACTTTCGCTTTCCCCCTCCCTATTGCCACGGCGGAACTCATCGCCGCCTGCCTTGCCC
GCTGCTGGACAGGGGCTCGGCTGTTGGGCACTGACAATTCCGTGGTGTTGTCGGGGA
AATCATCGTCCTTTCCTTGGCTGCTCGCCTGTGTTGCCACCTGGATTCTGCGCGGGAC
GTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCT
CCCTTTGGGCCGCCTCCCCGCCTAAGCTTATCGATACCGTCGAGATCTAACTTGTTTA
TTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
GTCTGGATCTCGACCTCGACTAGAGCATGGCTACGTAGATAAGTAGCATGGCGGGTT
AATCATTAACTACAAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCC
GGGCGGCCTCAGTGAGCGAGCGAGCGCGCCAGCTGGCGTAATAGCGAAGAGGCCC
GCACCGATCGCCCTTCCCAACAGTTGCGCAGCCTGAATGGCGAATGGAATTCCAGA
CGATTGAGCGTCAAAATGTAGGTATTTCCATGAGCGTTTTTCCTGTTGCAATGGCTG
GCGGTAATATTGTTCTGGATATTACCAGCAAGGCCGATAGTTTGAGTTCTTCTACTC
AGGCAAGTGATGTTATTACTAATCAAAGAAGTATTGCGACAACGGTTAATTTGCGTG
ATGGACAGACTCTTTTACTCGGTGGCCTCACTGATTATAAAAACACTTCTCAGGATT
CTGGCGTACCGTTCCTGTCTAAAATCCCTTTAATCGGCCTCCTGTTTAGCTCCCGCTC
TGATTCTAACGAGGAAAGCACGTTATACGTGCTCGTCAAAGCAACCATAGTACGCG
CCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGA
TTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTT
GCTTATACAATCTTCCTGTTTTTGGGGCTTTTCTGATTATCAACCGGGGTACATATGA
TTGACATGCTAGTTTTACGATTACCGTTCATCGATTCTCTTGTTTGCTCCAGACTCTC
AGGCAATGACCTGATAGCCTTTGTAGAGACCTCTCAAAAATAGCTACCCTCTCCGGC
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACCCG
```

-continued

```
CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGAC

CAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC
```

-continued

```
CCGCCATGCTACTTATCTACGTAGCCATGCTCTAGGACATTGATTATTGACTAGTGG
AGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTA
CGTATTAGTCATCGCTATTACCATGGTCGAGGTGAGCCCCACGTTCTGCTTCACTCTC
CCCATCTCCCCCCCCTCCCCACCCCCAATTTTGTATTTATTTATTTTTAATTATTTTG
TGCAGCGATGGGGGCGGGGGGGGGGGGGCGCGCGCCAGGCGGGGCGGGGGGG
GCGAGGGGCGGGGCGGGGCGAGGCGGAGAGGTGCGGCGGCAGCCAATCAGAGCGG
CGCGCTCCGAAAGTTTCCTTTTATGGCGAGGCGGCGGCGGCGGCGGCCCTATAAAA
AGCGAAGCGCGCGGCGGGCGGGAGTCGCTGCGCGCTGCCTTCGCCCCGTGCCCCGC
TCCGCCGCCGCCTCGCGCCGCCCGCCCCGGCTCTGACTGACCGCGTTACTAAAACAG
GTAAGTCCGGCCTCCGCGCCGGGTTTTGGCGCCTCCCGCGGGCGCCCCCCTCCTCAC
GGCGAGCGCTGCCACGTCAGACGAAGGGCGCAGCGAGCGTCCTGATCCTTCCGCCC
GGACGCTCAGGACAGCGGCCCGCTGCTCATAAGACTCGGCCTTAGAACCCCAGTAT
CAGCAGAAGGACATTTTAGGACGGGACTTGGGTGACTCTAGGGCACTGGTTTTCTTT
CCAGAGAGCGGAACAGGCGAGGAAAAGTAGTCCCTTCTCGGCGATTCTGCGGAGGG
ATCTCCGTGGGCGGTGAACGCCGATGATGCCTCTACTAACCATGTTCATGTTTTCTT
TTTTTTTCTACAGGTCCTGGGTGACGAACAGGGTACCGCCACCATGAGGGGCATGAA
GCTGCTGGGGCGCTGCTGGCACTGGCGGCCCTACTGCAGGGGCCGTGTCCCTGA
AGATCGCAGCCTTCAACATCCAGACATTTGGGGAGACCAAGATGTCCAATGCCACC
CTCGTCAGCTACATTGTGCAGATCCTGAGCCGCTATGACATCGCCCTGGTCCAGGAG
GTCAGAGACAGCCACCTGACTGCCGTGGGGAAGCTGCTGGACAACCTCAATCAGGA
TGCACCAGACACCTATCACTACGTGGTCAGTGAGCCACTGGGACGGAACAGCTATA
AGGAGCGCTACCTGTTCGTGTACAGGCCTGACCAGGTGTCTGCGGTGGACAGCTACT
ACTACGATGATGGCTGCGAGCCCTGCGGGAACGACACCTTCAACCGAGAGCCAGCC
ATTGTCAGGTTCTTCTCCCGGTTCACAGAGGTCAGGGAGTTTGCCATTGTTCCCCTGC
ATGCGGCCCCGGGGGACGCAGTAGCCGAGATCGACGCTCTCTATGACGTCTACCTG
GATGTCCAAGAGAAATGGGGCTTGGAGGACGTCATGTTGATGGGCGACTTCAATGC
GGGCTGCAGCTATGTGAGACCCTCCCAGTGGTCATCCATCCGCCTGTGGACAAGCCC
CACCTTCCAGTGGCTGATCCCCGACAGCGCTGACACCACAGCTACACCCACGCACTG
TGCCTATGACAGGATCGTGGTTGCAGGGATGCTGCTCCGAGGCGCCGTTGTTCCCGA
CTCGGCTCTTCCCTTTAACTTCCAGGCTGCCTATGGCCTGAGTGACCAACTGGCCCA
AGCCATCAGTGACCACTATCCAGTGGAGGTGATGCTGAAGGGCGGATCAGGCGGAT
CACCCAAATCTTGTGACAAAACTCACACATGCCCACCGTGCCCAGCACCTGAACTCC
TGGGGGGACCGTCAGTCTTCCTCTTCCCCCCAAAACCCAAGGACACCCTCATGATCT
CCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCC
GCGGGAGGAGCAGTACAACAGCACGTACCGTGTGGTCAGCGTCCTCACCGTCCTGC
```

-continued

ACCAGGACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGAACCACA

GGTGTACACCCTGCCCCCATCCCGGGAGGAGATGACCAAGAACCAGGTCAGCCTGA

CCTGCCTGGTCAAAGGCTTCTATCCCAGCGACATCGCCGTGGAGTGGGAGAGCAAT

GGGCAGCCGGAGAACAACTACAAGACCACGCCTCCCGTGCTGGACTCCGACGGCTC

CTTCTTCCTCTACAGCAAGCTCACCGTGGACAAGAGCAGGTGGCAGCAGGGGAACG

TCTTCTCATGCTCCGTGATGCATGAGGCTCTGCACAACCACTACACGCAGAAGAGCC

TCTCCCTGTCTCCGGGTAAATAG

3'

SEQ ID NO: 8 = SEQ ID NO: 1 + SEQ ID NO: 3
5'

TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

-continued

```
TTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTT
GCTTATACAATCTTCCTGTTTTTGGGGCTTTTCTGATTATCAACCGGGGTACATATGA
TTGACATGCTAGTTTTACGATTACCGTTCATCGATTCTCTTGTTTGCTCCAGACTCTC
AGGCAATGACCTGATAGCCTTTGTAGAGACCTCTCAAAAATAGCTACCCTCTCCGGC
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
```

-continued

```
TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGCGGGGGGGGGGGGGCGCGCGCCAGGCGGGGCGGGGGGGG

GCGAGGGGGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACCGCCACCGCCAGACCCTGCCG

TGCATTTATTTTTGGGGCGGCCTGCTGCCGTTTGGCATGCTGTGCGCGAGCAGCACC

ACCAAATGCACCGTGAGCCATGAAGTGGCGGATTGCAGCCATCTGAAACTGACCCA

GGTGCCGGATGATCTGCCGACCAACATTACCGTGCTGAACCTGACCCATAACCAGCT

GCGCCGCCTGCCGGCGGCGAACTTTACCCGCTATAGCCAGCTGACCAGCCTGGATGT

GGGCTTTAACACCATTAGCAAACTGGAACCGGAACTGTGCCAGAAACTGCCGATGC

TGAAAGTGCTGAACCTGCAGCATAACGAACTGAGCCAGCTGAGCGATAAAACCTTT

GCGTTTTGCACCAACCTGACCGAACTGCATCTGATGAGCAACAGCATTCAGAAAATT

AAAAACAACCCGTTTGTGAAACAGAAAAACCTGATTACCCTGGATCTGAGCCATAA
```

-continued

```
CGGCCTGAGCAGCACCAAACTGGGCACCCAGGTGCAGCTGGAAACCTGCAGGAAC

TGCTGCTGAGCAACAACAAAATTCAGGCGCTGAAAAGCGAAGAACTGGATATTTTT

GCGAACAGCAGCCTGAAAAAACTGGAACTGAGCAGCAACCAGATTAAAGAATTTAG

CCCGGGCTGCTTTCATGCGATTGGCCGCCTGTTTGGCCTGTTTCTGAACAACGTGCA

GCTGGGCCCGAGCCTGACCGAAAAACTGTGCCTGGAACTGGCGAACACCAGCATTC

GCAACCTGAGCCTGAGCAACAGCCAGCTGAGCACCACCAGCAACACCACCTTTCTG

GGCCTGAAATGGACCAACCTGACCATGCTGGATCTGAGCTATAACAACCTGAACGT

GGTGGGCAACGATAGCTTTGCGTGGCTGCCGCAGCTGGAATATTTTTTTCTGGAATA

TAACAACATTCAGCATCTGTTTAGCCATAGCCTGCATGGCCTGTTTAACGTGCGCTA

TCTGAACCTGAAACGCAGCTTTACCAAACAGAGCATTAGCCTGGCGAGCCTGCCGA

AAATTGATGATTTTAGCTTTCAGTGGCTGAAATGCCTGGAACATCTGAACATGGAAG

ATAACGATATTCCGGGCATTAAAAGCAACATGTTTACCGGCCTGATTAACCTGAAAT

ATCTGAGCCTGAGCAACAGCTTTACCAGCCTGCGCACCCTGACCAACGAAACCTTTG

TGAGCCTGGCGCATAGCCCGCTGCATATTCTGAACCTGACCAAAACAAAATTAGC

AAAATTGAAAGCGATGCGTTTAGCTGGCTGGGCCATCTGGAAGTGCTGGATCTGGG

CCTGAACGAAATTGGCCAGGAACTGACCGGCCAGGAATGGCGCGGCCTGGAAAACA

TTTTTGAAATTTATCTGAGCTATAACAAATATCTGCAGCTGACCCGCAACAGCTTTG

CGCTGGTGCCGAGCCTGCAGCGCCTGATGCTGCGCCGCGTGGCGCTGAAAAACGTG

GATAGCAGCCCGAGCCCGTTTCAGCCGCTGCGCAACCTGACCATTCTGGATCTGAGC

AACAACAACATTGCGAACATTAACGATGATATGCTGGAAGGCCTGGAAAAACTGGA

AATTCTGGATCTGCAGCATAACAACCTGGCGCGCCTGTGGAAACATGCGAACCCGG

GCGGCCCGATTTATTTTCTGAAAGGCCTGAGCCATCTGCATATTCTGAACCTGGAAA

GCAACGGCTTTGATGAAATTCCGGTGGAAGTGTTTAAAGATCTGTTTGAACTGAAAA

TTATTGATCTGGGCCTGAACAACCTGAACACCCTGCCGGCGAGCGTGTTTAACAACC

AGGTGAGCCTGAAAAGCCTGAACCTGCAGAAAAACCTGATTACCAGCGTGGAAAAA

AAAGTGTTTGGCCCGGCGTTTCGCAACCTGACCGAACTGGATATGCGCTTTAACCCG

TTTGATTGCACCTGCGAAAGCATTGCGTGGTTTGTGAACTGGATTAACGAAACCCAT

ACCAACATTCCGGAACTGAGCAGCCATTATCTGTGCAACACCCCGCCGCATTATCAT

GGCTTTCCGGTGCGCCTGTTTGATACCAGCAGCTGCAAAGATAGCGCGCCGTTTGAA

CTGTTTTTTATGATTAACACCAGCATTCTGCTGATTTTTATTTTATTGTGCTGCTGAT

TCATTTTGAAGGCTGGCGCATTAGCTTTTATTGGAACGTGAGCGTGCATCGCGTGCT

GGGCTTTAAAGAAATTGATCGCCAGACCGAACAGTTTGAATATGCGGCGTATATTAT

TCATGCGTATAAAGATAAAGATTGGGTGTGGGAACATTTTAGCAGCATGGAAAAAG

AAGATCAGAGCCTGAAATTTTGCCTGGAAGAACGCGATTTTGAAGCGGGCGTGTTTG

AACTGGAAGCGATTGTGAACAGCATTAAACGCAGCCGCAAAATTATTTTTGTGATTA

CCCATCATCTGCTGAAAGATCCGCTGTGCAAACGCTTTAAAGTGCATCATGCGGTGC

AGCAGGCGATTGAACAGAACCTGGATAGCATTATTCTGGTGTTTCTGGAAGAAATTC

CGGATTATAAACTGAACCATGCGCTGTGCCTGCGCCGCGGCATGTTTAAAGCCATT

GCATTCTGAACTGGCCGGTGCAGAAAGAACGCATTGGCGCGTTTCGCCATAAACTGC

AGGTGGCGCTGGGCAGCAAAAACAGCGTGCATGGGCGGATCAGGCGGATCACCCA

AATCTTGTGACAAAACTCACACATGCCCACCGTGCCCAGCACCTGAACTCCTGGGGG
```

-continued

```
GACCGTCAGTCTTCCTCTTCCCCCCAAAACCCAAGGACACCCTCATGATCTCCCGGA

CCCCTGAGGTCACATGCGTGGTGGTGGACGTGAGCCACGAAGACCCTGAGGTCAAG

TTCAACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTCCCAGCC

CCCATCGAGAAAACCATCTCCAAAGCCAAAGGGCAGCCCCGAGAACCACAGGTGTA

CACCCTGCCCCCATCCCGGGAGGAGATGACCAAGAACCAGGTCAGCCTGACCTGCC

TGGTCAAAGGCTTCTATCCCAGCGACATCGCCGTGGAGTGGGAGAGCAATGGGCAG

CCGGAGAACAACTACAAGACCACGCCTCCCGTGCTGGACTCCGACGGCTCCTTCTTC

CTCTACAGCAAGCTCACCGTGGACAAGAGCAGGTGGCAGCAGGGGAACGTCTTCTC

ATGCTCCGTGATGCATGAGGCTCTGCACAACCACTACACGCAGAAGAGCCTCTCCCT

GTCTCCGGGTAAATAG
```
3'

SEQ ID NO: 9 = SEQ ID NO: 1 + SEQ ID NO: 4
5'

```
TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC
```

-continued

```
ACGTTCGCCGGCTTTCCCCGTCAAGCTCTAAATCGGGGGCTCCCTTTAGGGTTCCGA
TTTAGTGCTTTACGGCACCTCGACCCCAAAAAACTTGATTAGGGTGATGGTTCACGT
AGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTT
GCTTATACAATCTTCCTGTTTTTGGGGCTTTTCTGATTATCAACCGGGGTACATATGA
TTGACATGCTAGTTTTACGATTACCGTTCATCGATTCTCTTGTTTGCTCCAGACTCTC
AGGCAATGACCTGATAGCCTTTGTAGAGACCTCTCAAAAATAGCTACCCTCTCCGGC
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
```

-continued

```
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGG
AGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGT
TGGCCGATTCATTAATGCAGCAGCTGCGCGCTCGCTCGCTCACTGAGGCCGCCCGGG
CAAAGCCCGGGCGTCGGGCGACCTTTGGTCGCCCGGCCTCAGTGAGCGAGCGAGCG
CGCAGAGAGGGAGTGGCCAACTCCATCACTAGGGGTTCCTTGTAGTTAATGATTAAC
CCGCCATGCTACTTATCTACGTAGCCATGCTCTAGGACATTGATTATTGACTAGTGG
AGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTA
CGTATTAGTCATCGCTATTACCATGGTCGAGGTGAGCCCCACGTTCTGCTTCACTCTC
CCCATCTCCCCCCCCTCCCCACCCCCAATTTTGTATTTATTTATTTTTTAATTATTTTG
TGCAGCGATGGGGGCGGGGGGGGGGGGGCGCGCGCCAGGCGGGGCGGGGGGG
GCGAGGGGCGGGGCGGGGCGAGGCGGAGAGGTGCGGCGGCAGCCAATCAGAGCGG
CGCGCTCCGAAAGTTTCCTTTTATGGCGAGGCGGCGGCGGCGGCCCTATAAAA
AGCGAAGCGCGCGGCGGGCGGGAGTCGCTGCGCGCTGCCTTCGCCCCGTGCCCCGC
TCCGCCGCCGCCTCGCGCCGCCCGCCCCGGCTCTGACTGACCGCGTTACTAAAACAG
GTAAGTCCGGCCTCCGCGCCGGGTTTTGGCGCCTCCCGCGGGCGCCCCCCTCCTCAC
GGCGAGCGCTGCCACGTCAGACGAAGGGCGCAGCGAGCGTCCTGATCCTTCCGCCC
GGACGCTCAGGACAGCGGCCCGCTGCTCATAAGACTCGGCCTTAGAACCCCAGTAT
CAGCAGAAGGACATTTTAGGACGGGACTTGGGTGACTCTAGGGCACTGGTTTTCTTT
CCAGAGAGCGGAACAGGCGAGGAAAAGTAGTCCCTTCTCGGCGATTCTGCGGAGGG
ATCTCCGTGGGCGGTGAACGCCGATGATGCCTCTACTAACCATGTTCATGTTTTCTT
TTTTTTTCTACAGGTCCTGGGTGACGAACAGGGTACCGCCACCATGAGGGGCATGAA
GCTGCTGGGGCGCTGCTGGCACTGGCGGCCCTACTGCAGGGGCCGTGTCCATGG
GCTTTTGCCGCAGCGCGCTGCATCCGCTGAGCCTGCTGGTGCAGGCGATTATGCTGG
CGATGACCCTGGCGCTGGGCACCCTGCCGGCGTTTCTGCCGTGCGAACTGCAGCCGC
ATGGCCTGGTGAACTGCAACTGGCTGTTTCTGAAAAGCGTGCCGCATTTTAGCATGG
```

-continued

```
CGGCGCCGCGCGGCAACGTGACCAGCCTGAGCCTGAGCAGCAACCGCATTCATCAT
CTGCATGATAGCGATTTTGCGCATCTGCCGAGCCTGCGCCATCTGAACCTGAAATGG
AACTGCCCGCCGGTGGGCCTGAGCCCGATGCATTTTCCGTGCCATATGACCATTGAA
CCGAGCACCTTTCTGGCGGTGCCGACCCTGGAAGAACTGAACCTGAGCTATAACAA
CATTATGACCGTGCCGGCGCTGCCGAAAAGCCTGATTAGCCTGAGCCTGAGCCATAC
CAACATTCTGATGCTGGATAGCGCGAGCCTGGCGGGCCTGCATGCGCTGCGCTTTCT
GTTTATGGATGGCAACTGCTATTATAAAAACCCGTGCCGCCAGGCGCTGGAAGTGGC
GCCGGGCGCGCTGCTGGGCCTGGGCAACCTGACCCATCTGAGCCTGAAATATAACA
ACCTGACCGTGGTGCCGCGCAACCTGCCGAGCAGCCTGGAATATCTGCTGCTGAGCT
ATAACCGCATTGTGAAACTGGCGCCGGAAGATCTGGCGAACCTGACCGCGCTGCGC
GTGCTGGATGTGGGCGGCAACTGCCGCCGCTGCGATCATGCGCCGAACCCGTGCAT
GGAATGCCCGCGCCATTTTCCGCAGCTGCATCCGGATACCTTTAGCCATCTGAGCCG
CCTGGAAGGCCTGGTGCTGAAAGATAGCAGCCTGAGCTGGCTGAACGCGAGCTGGT
TTCGCGGCCTGGGCAACCTGCGCGTGCTGGATCTGAGCGAAAACTTTCTGTATAAAT
GCATTACCAAAACCAAAGCGTTTCAGGGCCTGACCCAGCTGCGCAAACTGAACCTG
AGCTTTAACTATCAGAAACGCGTGAGCTTTGCGCATCTGAGCCTGGCGCCGAGCTTT
GGCAGCCTGGTGGCGCTGAAAGAACTGGATATGCATGGCATTTTTTTCGCAGCCTG
GATGAAACCACCCTGCGCCCGCTGGCGCGCCTGCCGATGCTGCAGACCCTGCGCCTG
CAGATGAACTTTATTAACCAGGCGCAGCTGGGCATTTTTCGCGCGTTTCCGGGCCTG
CGCTATGTGGATCTGAGCGATAACCGCATTAGCGGCGCGAGCGAACTGACCGCGAC
CATGGGCGAAGCGGATGGCGGCGAAAAAGTGTGGCTGCAGCCGGGCGATCTGGCGC
CGGCGCCGGTGGATACCCCGAGCAGCGAAGATTTTCGCCCGAACTGCAGCACCCTG
AACTTTACCCTGGATCTGAGCCGCAACAACCTGGTGACCGTGCAGCCGGAAATGTTT
GCGCAGCTGAGCCATCTGCAGTGCCTGCGCCTGAGCCATAACTGCATTAGCCAGGC
GGTGAACGGCAGCCAGTTTCTGCCGCTGACCGGCCTGCAGGTGCTGGATCTGAGCC
ATAACAAACTGGATCTGTATCATGAACATAGCTTTACCGAACTGCCGCGCCTGGAAG
CGCTGGATCTGAGCTATAACAGCCAGCCGTTTGGCATGCAGGGCGTGGGCCATAACT
TTAGCTTTGTGGCGCATCTGCGCACCCTGCGCCATCTGAGCCTGGCGCATAACAACA
TTCATAGCCAGGTGAGCCAGCAGCTGTGCAGCACCAGCCTGCGCGCGCTGGATTTTA
GCGGCAACGCGCTGGGCCATATGTGGGCGGAAGGCGATCTGTATCTGCATTTTTTTC
AGGGCCTGAGCGGCCTGATTTGGCTGGATCTGAGCCAGAACCGCCTGCATACCCTGC
TGCCGCAGACCCTGCGCAACCTGCCGAAAAGCCTGCAGGTGCTGCGCCTGCGCGAT
AACTATCTGGCGTTTTTTAAATGGTGGAGCCTGCATTTTCTGCCGAAACTGGAAGTG
CTGGATCTGGCGGGCAACCAGCTGAAAGCGCTGACCAACGGCAGCCTGCCGGCGGG
CACCCGCCTGCGCCGCCTGGATGTGAGCTGCAACAGCATTAGCTTTGTGGCGCCGGG
CTTTTTTAGCAAAGCGAAAGAACTGCGCGAACTGAACCTGAGCGCGAACGCGCTGA
AAACCGTGGATCATAGCTGGTTTGGCCCGCTGGCGAGCGCGCTGCAGATTCTGGATG
TGAGCGCGAACCCGCTGCATTGCGCGTGCGGCGCGGCGTTTATGGATTTTCTGCTGG
AAGTGCAGGCGGCGGTGCCGGGCCTGCCGAGCCGCGTGAAATGCGGCAGCCCGGGC
CAGCTGCAGGGCCTGAGCATTTTTGCGCAGGATCTGCGCCTGTGCCTGGATGAAGCG
```

-continued

```
CTGAGCTGGGATTGCTTTGCGCTGAGCCTGCTGGCGGTGGCGCTGGGCCTGGGCGTG
CCGATGCTGCATCATCTGTGCGGCTGGGATCTGTGGTATTGCTTTCATCTGTGCCTGG
CGTGGCTGCCGTGGCGCGGCCGCCAGAGCGGCCGCGATGAAGATGCGCTGCCGTAT
GATGCGTTTGTGGTGTTTGATAAAACCCAGAGCGCGGTGGCGGATTGGGTGTATAAC
GAACTGCGCGGCCAGCTGGAAGAATGCCGCGGCCGCTGGGCGCTGCGCCTGTGCCT
GGAAGAACGCGATTGGCTGCCGGGCAAAACCCTGTTTGAAAACCTGTGGGCGAGCG
TGTATGGCAGCCGCAAAACCCTGTTTGTGCTGGCGCATACCGATCGCGTGAGCGGCC
TGCTGCGCGAGCTTTCTGCTGGCGCAGCAGCGCCTGCTGGAAGATCGCAAAGAT
GTGGTGGTGCTGGTGATTCTGAGCCCGGATGGCCGCCGCAGCCGCTATGTGCGCCTG
CGCCAGCGCCTGTGCCGCCAGAGCGTGCTGCTGTGGCCGCATCAGCCGAGCGGCCA
GCGCAGCTTTTGGGCGCAGCTGGGCATGGCGCTGACCCGCGATAACCATCATTTTTA
TAACCGCAACTTTTGCCAGGGCCCGACCGCGGAAGGGCGGATCAGGCGGATCACCC
AAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAA
GTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAG
GACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGT
ACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTT
CCTCTACAGCAAGCTCACCGTGGACAAGAGCAGGTGGCAGCAGGGGAACGTCTTCT
CATGCTCCGTGATGCATGAGGCTCTGCACAACCACTACACGCAGAAGAGCCTCTCCC
TGTCTCCGGGTAAATAG
```
3'

SEQ ID NO: 10 = SEQ ID NO: 1 + SEQ ID NO: 5
5'

```
TTCTAGAATAATCAACCTCTGGATTACAAAATTTGTGAAAGATTGACTGGTATTCTT
AACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTGCTGTCT
CTTTATGAGGAGTTGTGGCCCGTTGTCAGGCAACGTGGCGTGGTGTGCACTGTGTTT
GCTGACGCAACCCCCACTGGTTGGGGCATTGCCACCACCTGTCAGCTCCTTTCCGGG
ACTTTCGCTTTCCCCCTCCCTATTGCCACGGCGGAACTCATCGCCGCCTGCCTTGCCC
GCTGCTGGACAGGGGCTCGGCTGTTGGGCACTGACAATTCCGTGGTGTTGTCGGGA
AATCATCGTCCTTTCCTTGGCTGCTCGCCTGTGTTGCCACCTGGATTCTGCGCGGGAC
GTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCT
CCCTTTGGGCCGCCTCCCCGCCTAAGCTTATCGATACCGTCGAGATCTAACTTGTTTA
TTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCAT
```

-continued

```
GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTGAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

CTTTATTGCTTAATTTTGCTAATTCTTTGCCTTGCCTGTATGATTTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG
```

-continued

```
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGG
AGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGT
TGGCCGATTCATTAATGCAGCAGCTGCGCGCTCGCTCGCTCACTGAGGCCGCCCGGG
CAAAGCCCGGGCGTCGGGCGACCTTTGGTCGCCCGGCCTCAGTGAGCGAGCGAGCG
CGCAGAGAGGGAGTGGCCAACTCCATCACTAGGGGTTCCTTGTAGTTAATGATTAAC
CCGCCATGCTACTTATCTACGTAGCCATGCTCTAGGACATTGATTATTGACTAGTGG
AGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTA
CGTATTAGTCATCGCTATTACCATGGTCGAGGTGAGCCCCACGTTCTGCTTCACTCTC
CCCATCTCCCCCCCCTCCCCACCCCCAATTTTGTATTTATTTATTTTTTAATTATTTTG
TGCAGCGATGGGGGCGGGGGGGGGGGGGCGCGCGCCAGGCGGGGCGGGGCGGG
GCGAGGGGCGGGGCGGGGCGAGGCGGAGAGGTGCGGCGGCAGCCAATCAGAGCGG
CGCGCTCCGAAAGTTTCCTTTTATGGCGAGGCGGCGGCGGCGGCGGCCCTATAAAA
```

-continued

```
AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGGCGGTGAACGCCGATGATGCCTCTACTAACCATGTTCATGTTTTCTT

TTTTTTTCTACAGGTCCTGGGTGACGAACAGGGTACCGCCACCATGAGGGGCATGAA

GCTGCTGGGGGCGCTGCTGGCACTGGCGGCCCTACTGCAGGGGGCCGTGTCCATGA

GCATGCTGTTTTATACCCTGATTACCGCGTTTCTGATTGGCATTCAGGCGGAACCGC

ATAGCGAAAGCAACGTGCCGGCGGGCCATACCATTCCGCAGGCGCATTGGACCAAA

CTGCAGCATAGCCTGGATACCGCGCTGCGCCGCGCGCAGCGCGCCGGCGGCGGC

GATTGCGGCGCGCGTGGCGGGCCAGACCCGCAACATTACCGTGGATCCGCGCCTGT

TTAAAAAACGCCGCCTGCGCAGCCCGCGCGTGCTGTTTAGCACCCAGCCGCCGCGC

GAAGCGGCGGATACCCAGGATCTGGATTTTGAAGTGGGCGGCGCGGCGCCGTTTAA

CCGCACCCATCGCAGCAAACGCAGCAGCAGCCATCCGATTTTTCATCGCGGCGAATT

TAGCGTGTGCGATAGCGTGAGCGTGTGGGTGGGCGATAAAACCACCGCGACCGATA

TTAAAGGCAAAGAAGTGATGGTGCTGGGCGAAGTGAACATTAACAACAGCGTGTTT

AAACAGTATTTTTTTGAAACCAAATGCCGCGATCCGAACCCGGTGGATAGCGGCTGC

CGCGGCATTGATAGCAAACATTGGAACAGCTATTGCACCACCACCCATACCTTTGTG

AAAGCGCTGACCATGGATGGCAAACAGGCGGCGTGGCGCTTTATTCGCATTGATAC

CGCGTGCGTGTGCGTGCTGAGCCGCAAAGCGGTGCGCCGCGCGGGCGGATCAGGCG

GATCACCCAAATCTTGTGACAAAACTCACACATGCCCACCGTGCCCAGCACCTGAAC

TCCTGGGGGACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCT

GAGGTCAAGTTCAACTGGTACGTGGACGGCGTGGAGGTGCATAATGCCAAGACAAA

GCCGCGGGAGGAGCAGTACAACAGCACGTACCGTGTGGTCAGCGTCCTCACCGTCC

TGCACCAGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCGAGAACC

ACAGGTGTACACCCTGCCCCCATCCCGGGAGGAGATGACCAAGAACCAGGTCAGCC

TGACCTGCCTGGTCAAAGGCTTCTATCCCAGCGACATCGCCGTGGAGTGGGAGAGC

AATGGGCAGCCGGAGAACAACTACAAGACCACGCCTCCCGTGCTGGACTCCGACGG

CTCCTTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAGAAGA

GCCTCTCCCTGTCTCCGGGTAAATAG

3'

SEQ ID NO: 11 = SEQ ID NO: 1 + SEQ ID NO: 6
5'

TTCTAGAATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG
```

-continued
```
CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTGAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

CTTTATTGCTTAATTTTGCTAATTCTTTGCCTTGCCTGTATGATTTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA
```

-continued

```
CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGAC

CAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC
```

-continued

```
CCGCCATGCTACTTATCTACGTAGCCATGCTCTAGGACATTGATTATTGACTAGTGG
AGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTT
TCCATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTA
CGTATTAGTCATCGCTATTACCATGGTCGAGGTGAGCCCCACGTTCTGCTTCACTCTC
CCCATCTCCCCCCCCTCCCCACCCCCAATTTTGTATTTATTTATTTTTTAATTATTTTG
TGCAGCGATGGGGGCGGGGGGGGGGGGGCGCGCGCCAGGCGGGGGGGGGGG
GCGAGGGGCGGGGCGGGGCGAGGCGGAGAGGTGCGGCGGCAGCCAATCAGAGCGG
CGCGCTCCGAAAGTTTCCTTTTATGGCGAGGCGGCGGCGGCGGCGGCCCTATAAAA
AGCGAAGCGCGCGGCGGGCGGGAGTCGCTGCGCGCTGCCTTCGCCCCGTGCCCCGC
TCCGCCGCCGCCTCGCGCCGCCCGCCCCGGCTCTGACTGACCGCGTTACTAAAACAG
GTAAGTCCGGCCTCCGCGCCGGGTTTTGGCGCCTCCCGCGGGCGCCCCCCTCCTCAC
GGCGAGCGCTGCCACGTCAGACGAAGGGCGCAGCGAGCGTCCTGATCCTTCCGCCC
GGACGCTCAGGACAGCGGCCCGCTGCTCATAAGACTCGGCCTTAGAACCCCAGTAT
CAGCAGAAGGACATTTTAGGACGGGACTTGGGTGACTCTAGGGCACTGGTTTTCTTT
CCAGAGAGCGGAACAGGCGAGGAAAAGTAGTCCCTTCTCGGCGATTCTGCGGAGGG
ATCTCCGTGGGCGGTGAACGCCGATGATGCCTCTACTAACCATGTTCATGTTTTCTT
TTTTTTTCTACAGGTCCTGGGTGACGAACAGGGTACCGCCACCATGAGGGGCATGAA
GCTGCTGGGGGCGCTGCTGGCACTGGCGGCCCTACTGCAGGGGGCCGTGTCCATGG
CGCTGTGGATGCGCCTGCTGCCGCTGCTGGCGCTGCTGGCGCTGTGGGCCCGGATC
CGGCGGCGGCGTTTGTGAACCAGCATCTGTGCGGCAGCCATCTGGTGGAAGCGCTGT
ATCTGGTGTGCGGCGAACGCGGCTTTTTTTATACCCCGAAAACCCGCCGCGAAGCGG
AAGATCTGCAGGTGGGCCAGGTGGAACTGGGCGGCGGCCCGGGCGCGGGCAGCCTG
CAGCCGCTGGCGCTGGAAGGCAGCCTGCAGAAACGCGGCATTGTGGAACAGTGCTG
CACCAGCATTTGCAGCCTGTATCAGCTGGAAAACTATTGCAACGGGCGGATCAGGC
GGATCACCCAAATCTTGTGACAAAACTCACACATGCCCACCGTGCCCAGCACCTGA
ACTCCTGGGGGGACCGTCAGTCTTCCTCTTCCCCCCAAAACCCAAGGACACCCTCAT
GATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGT
CCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAA
CCACAGGTGTACACCCTGCCCCCATCCCGGGAGGAGATGACCAAGAACCAGGTCAG
CCTGACCTGCCTGGTCAAAGGCTTCTATCCCAGCGACATCGCCGTGGAGTGGGAGA
GCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGG
GAACGTCTTCTCATGCTCCGTGATGCATGAGGCTCTGCACAACCACTACACGCAGAA
GAGCCTCTCCCTGTCTCCGGGTAAATAG
```

3'

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 7-11 or at the 5' end of SEQ ID NO. 1.

As will be appreciated by those skilled in the art, a perfect match of nucleotides with each of the miRNA expression cassette sequences is not necessary in order to have the desired result of increased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. An isolated plasmid comprising the nucleic acid sequence of SEQ ID NO: 3 encoding a messenger RNA (mRNA) encoding a fusion protein comprising an extracellular domain of a toll-like receptor 3 (TLR3) protein and an Fc domain.

2. The isolated plasmid of claim 1, wherein the isolated plasmid is inserted within one or more suitable pharmaceutically acceptable carriers.

3. An isolated plasmid comprising the nucleic acid sequence of SEQ ID NO: 8 encoding a messenger RNA (mRNA) encoding a fusion protein comprising an extracellular domain of a toll-like receptor 3 (TLR3) protein and an Fc domain.

* * * * *